US011462321B2

(12) United States Patent
Case et al.

(10) Patent No.: US 11,462,321 B2
(45) Date of Patent: Oct. 4, 2022

(54) MOBILE APPLICATIONS FOR BLOOD CENTERS

(75) Inventors: Brian C. Case, Lake Villa, IL (US); Jonathan Prendergast, Palatine, IL (US); John W. Barry, Jr., Mount Prospect, IL (US); Kyungyoon Min, Kildeer, IL (US); William H. Cork, Lake Bluff, IL (US); Daryl Richard Calhoun, Gurnee, IL (US); Christie Larson, Fox Lake, IL (US); Robert Bronersky, Highlands Ranch, CO (US)

(73) Assignee: FENWAL, INC., Lake Zurich, IL (US)

( * ) Notice: Subject to any disclaimer, the term of this patent is extended or adjusted under 35 U.S.C. 154(b) by 641 days.

(21) Appl. No.: 13/209,161

(22) Filed: Aug. 12, 2011

(65) Prior Publication Data
US 2012/0041777 A1 Feb. 16, 2012

Related U.S. Application Data

(60) Provisional application No. 61/373,197, filed on Aug. 12, 2010, provisional application No. 61/383,174, filed on Sep. 15, 2010.

(51) Int. Cl.
G06Q 10/08 (2012.01)
G16H 40/63 (2018.01)
(Continued)

(52) U.S. Cl.
CPC ........... *G16H 40/63* (2018.01); *G06Q 10/087* (2013.01); *G06Q 10/1093* (2013.01);
(Continued)

(58) Field of Classification Search
CPC ............ A61M 1/303; A61M 2230/005; A61M 2205/505; A61M 1/14; A61M 1/1603;
(Continued)

(56) References Cited

U.S. PATENT DOCUMENTS 4,605,503 A * 8/1986 Bilstad et al. ................ 210/651
5,153,827 A 10/1992 Coutre et al.
(Continued)

FOREIGN PATENT DOCUMENTS

CA 2846331 A1 9/2014
EP 1924307 B1 4/2012
(Continued)

OTHER PUBLICATIONS

Daniel C. McFarlane, Alexa K. Doig, James A. Agutter, Lara M. Brewer, Noah D. Syroid, Ranjeev Mittu, Faster clinical response to the onset of adverse events: A wearable metacognitive attention aid for nurse triage of clinical alarms, PLOS One, Published: May 16, 2018 (Year: 2018).*
(Continued)

*Primary Examiner* — Rachelle L Reichert
*Assistant Examiner* — Teresa S Williams
(74) *Attorney, Agent, or Firm* — Becker Patent Law, LLC

(57) ABSTRACT

Certain examples provide systems, methods, and apparatus to provide information regarding blood collection instruments via a mobile device. An example method for blood collection instrument management includes providing a graphical representation of one or more blood collection instruments with a visual indication of a status for each instrument. The graphical representation is to visually convey information regarding each of the one or more blood collection instruments and is selectable by a user to provide additional information regarding each of the one or more blood collection instruments. The method includes facilitating access to troubleshoot and interact with the one or more blood collection instruments via the mobile device. The method includes dynamically updating the status for each instrument via communication between the mobile device (Continued)

and one or more blood collection facilities at which the one or more blood collection instruments are located.

34 Claims, 24 Drawing Sheets

(51) Int. Cl.
  *G06T 11/20* (2006.01)
  *G16H 10/60* (2018.01)
  *G16H 40/67* (2018.01)
  *G06Q 10/10* (2012.01)

(52) U.S. Cl.
  CPC ........... *G06T 11/206* (2013.01); *G16H 10/60* (2018.01); *G16H 40/67* (2018.01)

(58) Field of Classification Search
  CPC ........ A61M 1/282; A61B 5/14; A61B 5/0022; A61B 5/15003; A61B 5/7445; A61B 5/742; A61B 5/0205; G06F 19/327; G06F 19/366; G16H 10/40; G16H 10/60; G16H 40/67; G16H 40/63; G16H 20/17; G16H 40/60; G01C 21/32; G01C 21/3667; G06Q 10/087; G06Q 10/1093; H04N 21/8173; H04N 21/47; H04N 21/42204; G06T 11/206
  USPC .......... 705/2, 3; 128/903; 709/220; 701/208, 701/461
  See application file for complete search history.

(56) References Cited

U.S. PATENT DOCUMENTS

| | | | |
|---|---|---|---|
| 6,256,643 B1* | 7/2001 | Cork et al. | |
| 6,488,029 B1 | 12/2002 | Hood et al. | |
| 6,540,672 B1* | 4/2003 | Simonsen .......... A61B 5/14532 128/903 |
| 6,542,910 B2* | 4/2003 | Cork et al. | |
| 6,571,128 B2 | 5/2003 | Lebel et al. | |
| 6,602,469 B1* | 8/2003 | Maus et al. ................... 422/68.1 |
| 6,613,566 B2 | 9/2003 | Kandler et al. | |
| 6,635,014 B2 | 10/2003 | Starkweather et al. | |
| 7,225,406 B2 | 5/2007 | Babula et al. | |
| 7,384,410 B2 | 6/2008 | Eggers et al. | |
| 7,815,602 B2 | 10/2010 | Mann et al. | |
| 7,861,122 B2* | 12/2010 | Cornwell et al. ............... 714/42 |
| 7,942,844 B2 | 5/2011 | Moberg et al. | |
| 8,038,593 B2* | 10/2011 | Friedman ............. A61B 5/0002 600/26 |
| 8,229,535 B2* | 7/2012 | Mensinger et al. .......... 600/345 |
| 8,234,128 B2* | 7/2012 | Martucci et al. ................ 705/3 |
| 8,255,238 B2 | 8/2012 | Powell et al. | |
| 8,285,328 B2 | 10/2012 | Caffey et al. | |
| 8,291,337 B2 | 10/2012 | Gannin et al. | |
| 8,485,828 B2 | 7/2013 | Cork | |
| 8,552,880 B2 | 10/2013 | Kopp et al. | |
| 8,645,154 B2 | 2/2014 | Eggers et al. | |
| 8,676,600 B2 | 3/2014 | Case et al. | |
| 2001/0044731 A1 | 11/2001 | Coffman et al. | |
| 2003/0004758 A1 | 1/2003 | Luttrell | |
| 2003/0040835 A1* | 2/2003 | Ng et al. ....................... 700/214 |
| 2003/0040938 A1* | 2/2003 | Ng ............................. A61B 5/14 705/2 |
| 2003/0093503 A1* | 5/2003 | Yamaki ............... G06F 19/3406 709/220 |
| 2003/0154108 A1 | 8/2003 | Fletcher-Haynes et al. | |
| 2004/0204837 A1 | 10/2004 | Singleton | |
| 2006/0031098 A1 | 2/2006 | Kalthoff | |
| 2006/0100746 A1 | 5/2006 | Leibner-Druska | |
| 2006/0116639 A1 | 6/2006 | Russell | |
| 2006/0229557 A1 | 10/2006 | Fathallah et al. | |
| 2007/0219826 A1 | 9/2007 | Brodsky | |
| 2008/0033744 A1 | 2/2008 | Jones | |
| 2008/0126969 A1 | 5/2008 | Blomquist | |
| 2008/0140452 A1 | 6/2008 | Seul et al. | |
| 2008/0172026 A1* | 7/2008 | Blomquist .......... G06F 19/3468 604/500 |
| 2009/0076856 A1 | 3/2009 | Darby et al. | |
| 2009/0153058 A1 | 6/2009 | Feng et al. | |
| 2009/0156991 A1* | 6/2009 | Roberts .................. G06F 19/327 604/67 |
| 2009/0163855 A1 | 6/2009 | Shin et al. | |
| 2009/0165236 A1 | 6/2009 | Gounares et al. | |
| 2009/0177992 A1 | 7/2009 | Rubalcaba et al. | |
| 2009/0217202 A1 | 8/2009 | Foley et al. | |
| 2009/0259408 A1 | 10/2009 | Mishima et al. | |
| 2009/0259493 A1* | 10/2009 | Venon ................... G06F 19/322 705/3 |
| 2009/0276345 A1 | 11/2009 | Hughes | |
| 2010/0017222 A1 | 1/2010 | Yeluri | |
| 2010/0049542 A1 | 2/2010 | Benjamin | |
| 2010/0131883 A1 | 5/2010 | Linthicum et al. | |
| 2011/0004835 A1* | 1/2011 | Yanchar ............... G06Q 10/109 715/763 |
| 2011/0137134 A1 | 6/2011 | Hemmerling et al. | |
| 2011/0167250 A1* | 7/2011 | Dicks ..................... G16H 40/67 713/2 |
| 2011/0185035 A1 | 7/2011 | Van | |
| 2011/0295749 A1 | 12/2011 | Scalisi | |
| 2012/0038651 A1 | 2/2012 | Case et al. | |
| 2012/0041777 A1 | 2/2012 | Case et al. | |
| 2012/0101847 A1 | 4/2012 | Johnson et al. | |
| 2012/0271655 A1 | 10/2012 | Knobel et al. | |
| 2014/0276571 A1 | 9/2014 | Ludolph | |
| 2014/0298022 A1 | 10/2014 | Proennecke et al. | |
| 2015/0186834 A1 | 7/2015 | Mickles et al. | |
| 2015/0356250 A1 | 12/2015 | Polimeni | |
| 2016/0210838 A1* | 7/2016 | Yan ....................... G08B 25/001 |

FOREIGN PATENT DOCUMENTS

| | | | | |
|---|---|---|---|---|
| EP | 2624157 | | 8/2013 | |
| GB | WO2016205212 A1 | * | 12/2016 | ............. G16H 50/20 |
| WO | WO2002080993 | | 10/2002 | |
| WO | WO 2012/075322 | * | 6/2012 | ............. G06Q 10/10 |
| WO | WO2016205212 | * | 12/2016 | |

OTHER PUBLICATIONS

Daniel C. McFarlane, Alexa K. Doig, James A. Agutter, Lara M. Brewer, Noah D. Syroid, Ranjeev Mittu, Faster clinical response to the onset of adverse events: A wearable metacognitive attention aid for nurse triage of clinical alarms, May 16, 2018, PLOS One Journal (Year: 2016).*

Looking Glass, "iGive Blood," iTunes App Store, http://itunes.apple.com/us/app/igive-blood/id330741267?mt=8, (Last Accessed Aug. 28, 2012).

Final Rejection dated Sep. 24, 2013 in U.S. Appl. No. 13/748,580.

Response to Office Action, dated Jul. 12, 2013, in U.S. Appl. No. 13/748,580.

Non-final Office Action dated Apr. 12, 2013 in U.S. Appl. No. 13/748,580.

Non-Final Office Action dated Nov. 3, 2014 in U.S. Appl. No. 13/748,580.

Amendment and Reply dated Jan. 30, 2015 in U.S. Appl. No. 13/748,580.

Notification Concerning Transmittal of International Preliminary Report on Patentability (IPRP), IPRP and Written Opinion of the International Searching Authority, International application No. PCT/US2013/022736, seven pages.

"iGive Blood on the App Store on iTunes," printed from https://itunes.apple.com/us/app/igive-blood/id330741267?mt=8, Jun. 3, 2015.

Velasco, Anna "Birmingham Firm's Software Aid Doctors Keep Track of Patients' Vital Signs," Everything Alabama, http://blog.al.com/living-news//print.html, Dec. 24, 2009.

Final Office Action dated May 18, 2015, U.S. Appl. No. 13/748,580, 20 pages.

(56) References Cited

OTHER PUBLICATIONS

Reply to Final Office Action in U.S. Appl. No. 13/748,580 dated Aug. 18, 2015.
Notice of Allowance in U.S. Appl. No. 13/209,161 dated Nov. 6, 2013, 10 pages.
Non-Final Office Action in U.S. Appl. No. 14/971,707 dated Apr. 6, 2016, 23 pages.
Appeal Brief, U.S. Appl. No. 13/748,580, dated Nov. 2017, 28 pages.
Examiner's Answer, U.S. Appl. No. 13/748,580, dated Jul. 27, 2016, 11 pages.
Reply Brief, U.S. Appl. No. 13/748,580, dated Aug. 18, 2016, 14 pages.
Appeal Brief, U.S. Appl. No. 15/641,917, dated Mar. 2, 2021, 27 pages.
Final Rejection, U.S. Appl. No. 15/641,917, dated Sept. 2, 2020, 28 pages.
Reply, U.S. Appl. No. 15/641,917, dated May 28, 2020, 20 pages.
Non-Final Rejection, U.S. Appl. No. 15/641,917, dated Feb. 28, 2020, 25 pages.
"Go for the Gold" website: http://web.archive.org/web/20090530103915/http://www.goforthegold.org/infopage.asp?page=30[ May 8, 2013 9:31:50 AM].
"The Blood Alliance" website, http://web.archive.org/web/20100528150632/http://www.igiveblood.com/[May 8, 2020 13 11:16:40 AM].
"The Blood Center" website, http://web.archive.org/web/20100514040706/http://www.thebloodcenter.org/[ May 8, 2013 9:39:57 AM].
Final Rejection in U.S. Appl. No. 15/641,917 dated Jun. 24, 2021, 31 pages.
BLOODR:_blood_donor_and_requester_mobile_application, Mhealth 2017; 3:40, Published online Sep. 18, 2017, Vamsi Krishna Tatikonda and Hosam El-Ocla (Year: 2017).
Notice of Allowance in U.S. Appl. No. 15/641,917 dated Apr. 28, 2022, 8 pages.

\* cited by examiner

Op C

MOBILE APPLICATIONS FOR BLOOD CENTERS

CROSS-REFERENCE TO RELATED APPLICATIONS

The present application relates and claims priority to U.S. provisional patent application Ser. No. 61/373,197, filed on Aug. 12, 2010, and U.S. provisional patent application, Ser. No. 61/383,174, filed on Sep. 15, 2010, each of which is herein incorporated by reference in its entirety.

FIELD

The present invention relates generally to methods, systems, and apparatus to provide mobile applications for donors, blood centers, and associated medical personnel.

BACKGROUND

Hospitals, clinics, and other healthcare providers continually face a need for donated blood to help in treating patients. It is often difficult to notify and educate the public regarding donations. Donors may not become repeat donors due to a lack of information and access. Operators and administrators may introduce inefficiencies in their operation and management of blood collection instruments due to a lack of information and access.

BRIEF SUMMARY

Certain examples provide systems, methods, and apparatus to provide information regarding blood collection instruments via a mobile device.

Certain examples provide a computer-implemented method for blood collection instrument management. The method includes providing a graphical representation of one or more blood collection instruments with a visual indication of a status for each instrument. The graphical representation is to visually convey information regarding each of the one or more blood collection instruments and is selectable by a user to provide additional information regarding each of the one or more blood collection instruments. The method includes facilitating access to troubleshoot and interact with the one or more blood collection instruments via the mobile device. The method includes dynamically updating the status for each instrument via communication between the mobile device and one or more blood collection facilities at which the one or more blood collection instruments are located.

Certain examples provide a tangible computer readable storage medium including program code for execution by a processor, the program code, when executed, to implement a method for blood collection instrument management. The method includes providing a graphical representation of one or more blood collection instruments with a visual indication of a status for each instrument. The graphical representation is to visually convey information regarding each of the one or more blood collection instruments and is selectable by a user to provide additional information regarding each of the one or more blood collection instruments. The method includes facilitating access to troubleshoot and interact with the one or more blood collection instruments via the mobile device. The method includes dynamically updating the status for each instrument via communication between the mobile device and one or more blood collection facilities at which the one or more blood collection instruments are located.

Certain examples provide a mobile blood collection instrument management system. The system includes a processor and memory storing instructions to display content and accept user input to implement, via a mobile device: a graphical representation of one or more blood collection instruments including a visual indication of a status for each instrument, the graphical representation to visually convey information regarding each of the one or more blood collection instruments and selectable by a user to provide additional information regarding each of the one or more blood collection instruments; and an executable application to provide access to troubleshoot and interact with the one or more blood collection instruments via a mobile device. The system is to dynamically update the status for each instrument via communication between the mobile device and one or more blood collection facilities at which the one or more blood collection instruments are located.

Certain examples provide a computer-implemented method for blood component tracking device. The method includes facilitating input of a donor identifier and a collection time for a collected blood component via a mobile device. The method includes recording an identifier associated with a container to transport the collected blood component for processing. The method includes tracking the container with the collected blood component via the mobile device affixed to the container during transit. The method includes providing the donor identifier, container identifier, collection time, and tracking information to a computer at a collection center for processing of the collected blood component.

Figure 1:
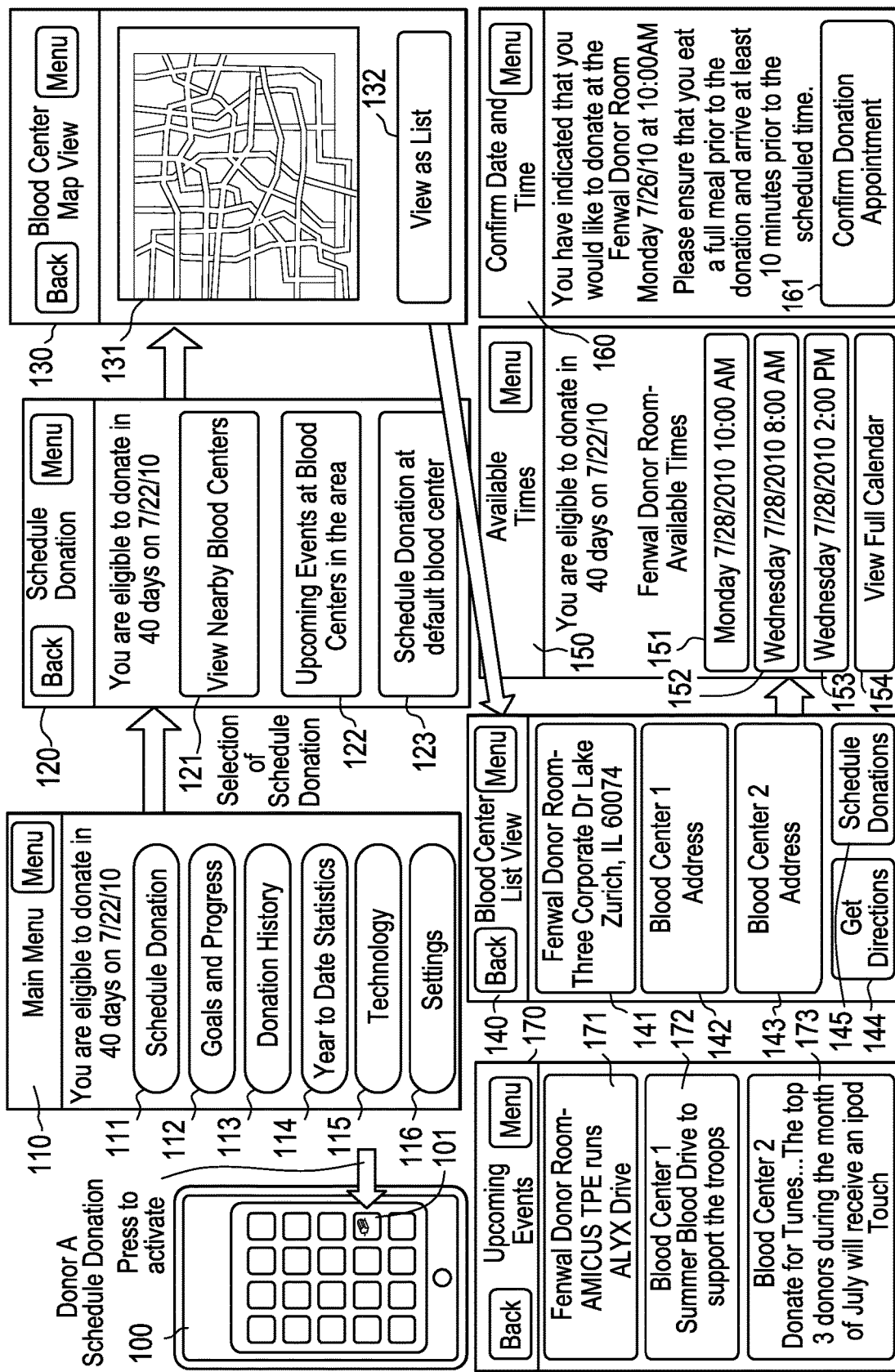
FIGS. 1-5 show example interfaces for current and/or potential blood donors.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DESCRIPTION OF CERTAIN EXAMPLES

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

It will be understood that the present invention may be embodied in other specific forms without departing from the spirit thereof. The present examples and embodiments, therefore, are to be considered in all respects as illustrative and not restrictive, and the invention is not to be limited to the details presented herein.

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

Certain examples provide mobile applications for blood centers that include donor, administration, operations, and/or service applications. Certain examples converge information into one application that helps provide improved record keeping, better donor experience, reduction of waste, and/or enhanced ease of use for the user, for example. In addition, flow of communication can be improved throughout the supply chain. Furthermore, certain examples help provide for automation of manual tasks which would eliminate or reduce potential user errors.

In certain examples, an application can provide training, feedback, monitor, and status information on a collection process. For example, an application on a mobile or handheld computing device (e.g., an Apple iPad™, iPhone™, and/or other tablet computer or smartphone) can help facilitate user training with respect to one or more blood collection and/or processing procedures. For example, use of equipment and supplies may be facilitated.

In certain examples, a customer may purchase an application and/or download the application to a device. Materials may be provided to explain the application, provide directions for downloading/installing the application onto a phone, and/or explain how to use the application. In some examples, an application can give visual assistance in operating a device such as Fenwal's Alyx™ or Amicus™ collection instrument. In some examples, the application may provide a mobile version of the operator's manual for the Alyx™ system and/or the Amicus™ separator.

In some examples, an application may make provider websites mobile-friendly. For example, Microsoft SharePoint™ supports mobile views and can be leveraged to provide a mobile-friendly provider (e.g., Fenwal) website.

In some examples, an application for use with a mobile device is integrated with a provider (e.g., Fenwal) data management system. In some examples, the application enables the device to be made 21 CFR part 11 compliant. In some examples, the application can be used across a variety of blood products.

Mobile Applications

In certain examples, an application can provide training, feedback, monitor, and status information on a collection process. For example, an application on a mobile or handheld computing device (e.g., an Apple iPad™, iPhone™, and/or other tablet computer or smartphone) can help facilitate user training with respect to one or more blood collection and/or processing procedures. For example, use of equipment and supplies may be facilitated.

In certain examples, a customer may purchase an application and/or download the application to a device. Materials may be provided to explain the application, provide directions for downloading/installing the application onto a phone, and/or explain how to use the application. In some examples, an application can give visual assistance in operating a device such as Fenwal's Alyx™ or Amicus™ collection instrument. In some examples, the application may provide a mobile version of the operator's manual for the Alyx™ system and/or the Amicus™ separator.

In some examples, an application may make provider websites mobile-friendly. For example, Microsoft SharePoint™ supports mobile views and can be leveraged to provide a mobile-friendly provider (e.g., Fenwal) website.

In some examples, an application for use with a mobile device is integrated with a provider (e.g., Fenwal) data management system. In some examples, the application enables the device to be made 21 CFR part 11 compliant. In some examples, the application can be used across a variety of blood products.

FIGS. 1-5 show example interfaces for current and/or potential blood donors (e.g., with respect to Donors A-E). For a donor, an example application can track donation history. The application can notify a donor when he/she is able/available (e.g., based on donation guideline eligibility and/or schedule availability) to donate. An example application can allow for the donor to enter donation goals, e.g., 30 liters, and provide a thermometer type of graph on the donor's progress to the goal. The goal graph can be broken down into smaller goals, for example. At each smaller goal, a pop up and/or other dialog box and/or indicator can be provided to explain how many people the donor helped (e.g., at five liters (5 L) a donor helps ten people that underwent emergency surgery, etc.). In some examples, donors can be shown incentives that can be received after a set amount of donations (e.g., 30 donations=$25 gas card, etc.). The application can also enable tracking of different blood components (e.g., red blood cells (RBC), plasma, platelets). For each component goal it would have the appropriate people helped (e.g. a donor's five units of platelets donated were used to help three chemotherapy patients. The application can also compare the donor to an average donor/donors (e.g., frequency of collections, units collected, etc.).

The application can enable a donor to post his/her goals and collections to a webpage, such as a Facebook™ page or Twitter™ account, etc. A webpage can also be provided to explain the donation process, the technology, why to donate, the benefits of a double red blood cell (2RBC) procedure versus whole blood collection, etc.

In certain examples, the application can provide locations for upcoming donations and/or can link with online (e.g., Google™) maps and/or directions. The application can also prioritize the donation locations that feature a particular (e.g., Fenwal™) technology and/or need a certain blood component, etc. In certain examples, based on tracking of a donor's location, a nearby donation facility can compare a current inventory (and associated need) with the tracked donor's information (e.g., blood type, eligibility, etc.)

In certain examples, announcements and/or requests can be pushed to a donor's mobile device by the donation facility. For example, information can be pushed to one or more donors based on donor specific characteristics, a need for a particular blood component and/or a relationship of the donor to the blood collection facility (e.g., donor blood type, donor characteristics, proximity, membership, registration, prior donation at the facility, etc.).

In certain examples, donor information can be pushed to a donation center and used information to send relevant information to the donor. For example, the donor's goal/progress/location information is pushed to a donation center computer, and then the donation center can send the donor reminders to donate. Alternatively or in addition, if there is a need for the donor's specific blood type, the donation center can send a user a specific message related to the donor's goals (e.g., please donate and you will reach your personal goal of x). News or human interest stories can also be sent to particular donors based on donor characteristics, need for blood, and/or a relationship to the blood collection facility, for example.

In certain examples, an application can provide feedback on the collection process. The application can diagram the procedure (e.g., arm to centrifuge to final product storage in real time). In certain examples, another part of the application can monitor flow rates of the vein with a game style interface with the donor trying to keep the flow rate in an optimal window. For example, the donor can squeeze a mobile computing device at specific intervals to control and/or optimize flow rate. The mobile computing device can indicate how well the donor is controlling the flow rate during the procedure based on an internal accelerometer, touch screen, and/or other suitable mechanism. This can also link up with other donors and they can "compete" against each other (e.g., akin to the carnival game of filling up a water balloon with water).

In certain examples, a blood collection/processing machine and/or a donor application communicates with a donor's mobile device (e.g., a phone) based on donor characteristic(s) and/or donor location. For example, after a donation, a donor's movement may need to be restricted for a certain period of time. If the donor does move, the donor's movement can be detected via the mobile device and/or other monitor, and the mobile device can generate and/or relay an alert (e.g., the mobile device can vibrate, sound an alarm, notify the blood donation center and/or blood collection machine, etc.). Thus, compliance with donation rules, guidelines, best practices, etc., can be facilitated via a mobile application.

In certain examples, an application enables a center to push announcements and upcoming events to donors. The application can provide links to enable the donor to schedule his or her donation and maps of locations where he or she can donate, for example. As discussed above, targeted donation requests and/or announcements can be pushed to a donor based on location, preference, eligibility, etc.

As illustrated, for example, in FIG. 1, a mobile computing device 100, such as a smart phone or tablet computer, etc., includes a donation application 101 that is selectable by a user via an interface of the device 100. The application 101 includes a menu 110 indicating, for example, a remaining time and date for next donation eligibility. The menu 110 includes one or more options for user selection including to schedule a donation 111, view goals and progress (toward the goal(s)) 112, view donation history 113, view year to date statistics 114, see available technology 115, and settings 116, for example.

Selecting to schedule a donation 111, for example, provides a donation scheduling interface 120. Via the donation scheduling interface 120, a user can view nearby blood center(s) 121, view upcoming events at blood centers in the area 122, schedule a donation at a default blood center 123, etc. The schedule donation option 111, 120 allows a user to schedule a donation based either on a default blood center 123 or via a search for blood centers in the area 121. The application can interface with a map service, such as Google Maps, to display nearby facilities and provide driving directions and/or operating hours for the facilities. In addition to scheduling appointments, the application can also display upcoming event(s) for blood center(s) in the vicinity.

For example, by selecting to view nearby blood centers 121 from the schedule donation menu 120, a blood center map view 130 is displayed. The map view 130 shown in the example of FIG. 1 provides a graphical map 131 and an option to view available blood center(s) as a list 132. For example, a user can select a blood center on the map 131 and will then be prompted to get directions or schedule an appointment.

In a blood center list view 140, shown for example in FIG. 1, a listing of available blood centers 141, 142, 143 within a certain area are provided for user selection. Via the interface 140, a user can get directions 144 or schedule a donation 145 for a selected blood center 141, 142, 143. By selecting to schedule a donation 145, a view of available times 150 is provided, which tells the user his or her next eligibility to donate and provides one or more available times 41, 142, 143 for a selected blood center. The user can select on any of the available times 151, 152, 153 or view a full calendar 154 showing the available times. By selecting a time 151, 152, 153, a confirmation screen 160 is provided to summarize the scheduled donation and provide instructions for the donation, for example. The user can then confirm the donation appointment 161. Selection of confirm the donation appointment 161 reserves the time at the selected blood center and sends an email to the user to confirm. The user can also receive an appointment to put in his or her electronic calendar, for example.

Additionally, by selecting to view upcoming events at blood centers in the area 122, a listing of upcoming events 170 can be provided. In certain examples, a user can select an event 171, 172, 173 to view additional information and/or register for an event.

Figure 2:
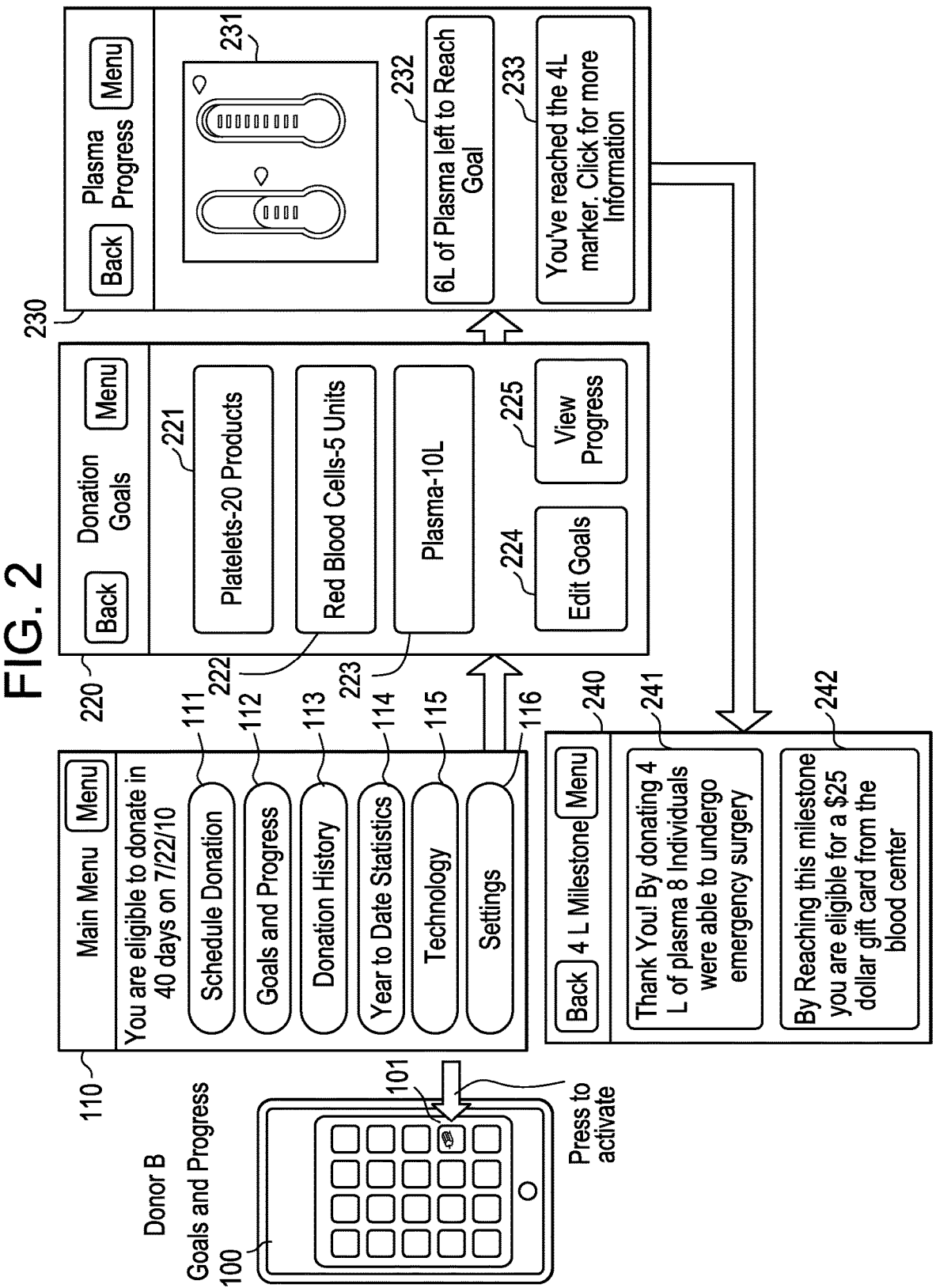

As illustrated, for example, in FIG. 2, selection of the goals and progress 112 option in the main menu 110 provides a donation goals screen 220. The donation goals 220 provide one or more blood component donation goals, such as platelets (e.g., 20 products) 221, red blood cells (e.g., 5 units) 222, plasma (e.g., 10 liters) 223, etc. The user can edit goals 224 and/or view progress 225. The edit and/or progress may be with respect to all goals, to one or more selected goals, etc. For example, by selecting the plasma goal 223 and selecting view progress 225, a plasma progress screen 230 is displayed.

The example plasma progress screen 230 provides a visual representation 231 of the user's current progress toward the plasma goal. Additionally, the progress view 230 provides an indication 232 of an amount of plasma remaining to reach the plasma goal. In the example of FIG. 2, if a milestone has been reached along the way to the goal, an indicator and option for additional information 233 may be provided. By selecting the option 233, a milestone screen 240 is displayed.

The milestone view 240 provides information 241 regarding use of donated blood product(s), as well as an incentive 242 provided to the user. For example, the user may be told 241 that his or her 4 liters of plasma donated have helped 8 individuals undergoing emergency surgery. An incentive 242 can also be provided, such as a $25 gift card from the blood center, for example. By selecting an incentive 242, a user can redeem the incentive. The redemption becomes active once the donor has achieved the milestone, for example. Multiple milestones can be listed and activated once achieved, for example. In certain examples, incentives and milestones can be compared between donors, pitting donors in a friendly competition or game to participate in blood donation and/or spread word of a need for donation of a blood component.

Thus, the goals and progress option 112 allows the user to set personal goals for different blood components. The goals are editable by the user. Progress can be tracked alphanumerically and/or graphically, such as using one or more thermometers tracking a rise toward the goal. The progress can show progress to an overall goal along with progress to one or more incremental goals. At various milestones (e.g., incremental goals), incentives can be awarded along with information regarding how the blood component(s) may have been used to help those in need (e.g., patients). In certain examples, collection goals can be integrated with social networking sites, such as Facebook™, Twitter™, etc.

Figure 3:
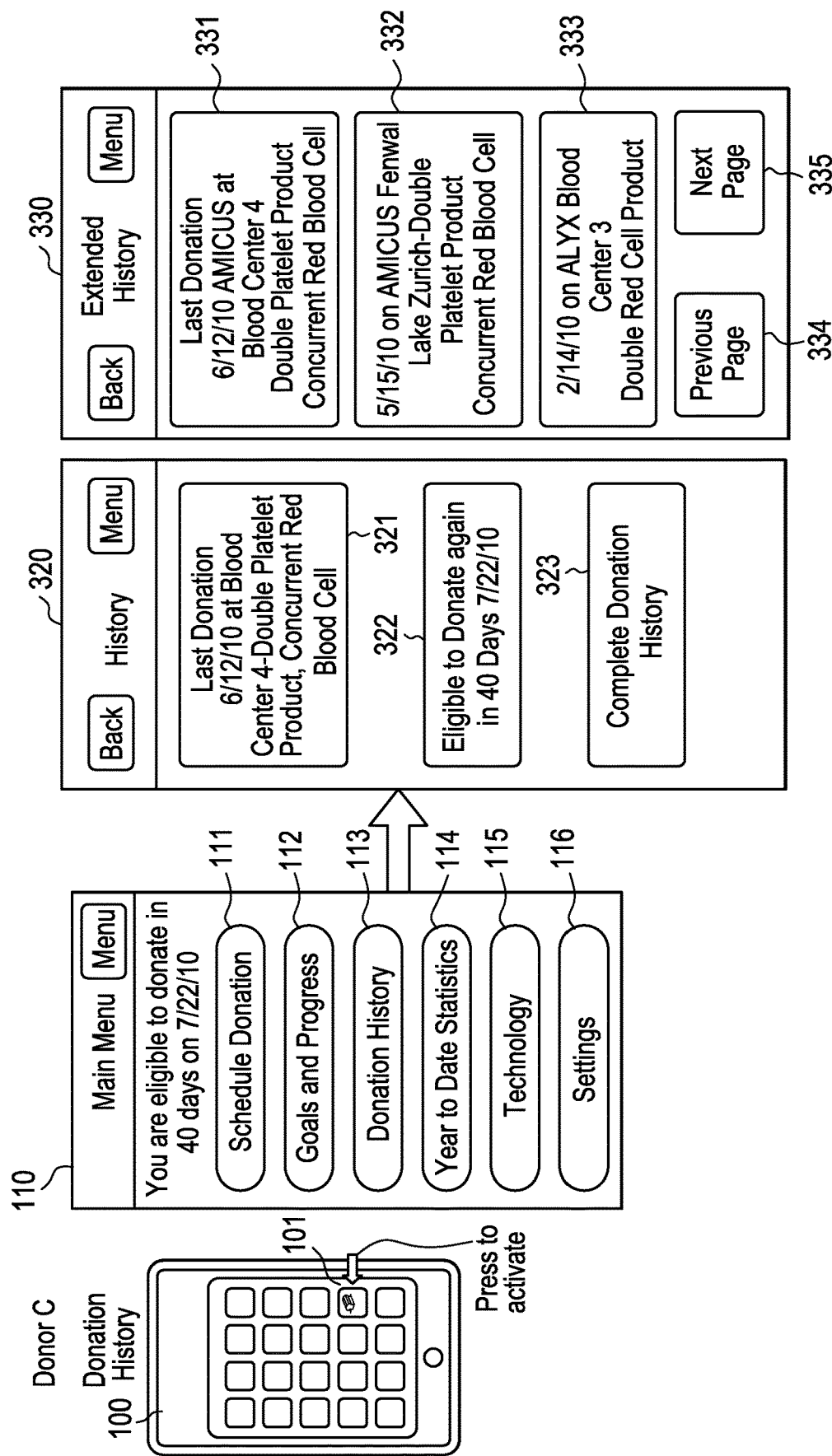

FIG. 3 depicts an example in which the donation history option 113 is selected from the main menu 110 of a blood donor application 101 on a mobile or other computing device 100. A history view 320 provides an indication of last donation 321, next donation eligibility 322, etc., along with a complete donation history 323, for example. Selecting the complete history option 323 provides an extended history view 330. The extended view 330 includes a last donation 331, as well as a number of prior donations 332, 333. If prior donations exceed viewable space, options to navigate a previous page 334 or a next page 335 may be provided, for example.

Selection of the donation history option 113 allows the user to see his or her last donation along with real time (or substantially real time given some system access, processing, and/or transmission delay) information regarding a remaining deferral period. The complete donation option 330 allows the user to view information such as where, when, what, how much, and on what device the user donated in the past. The donation history can also be integrated with social networking such as Facebook™, Twitter™, etc.

Figure 4:
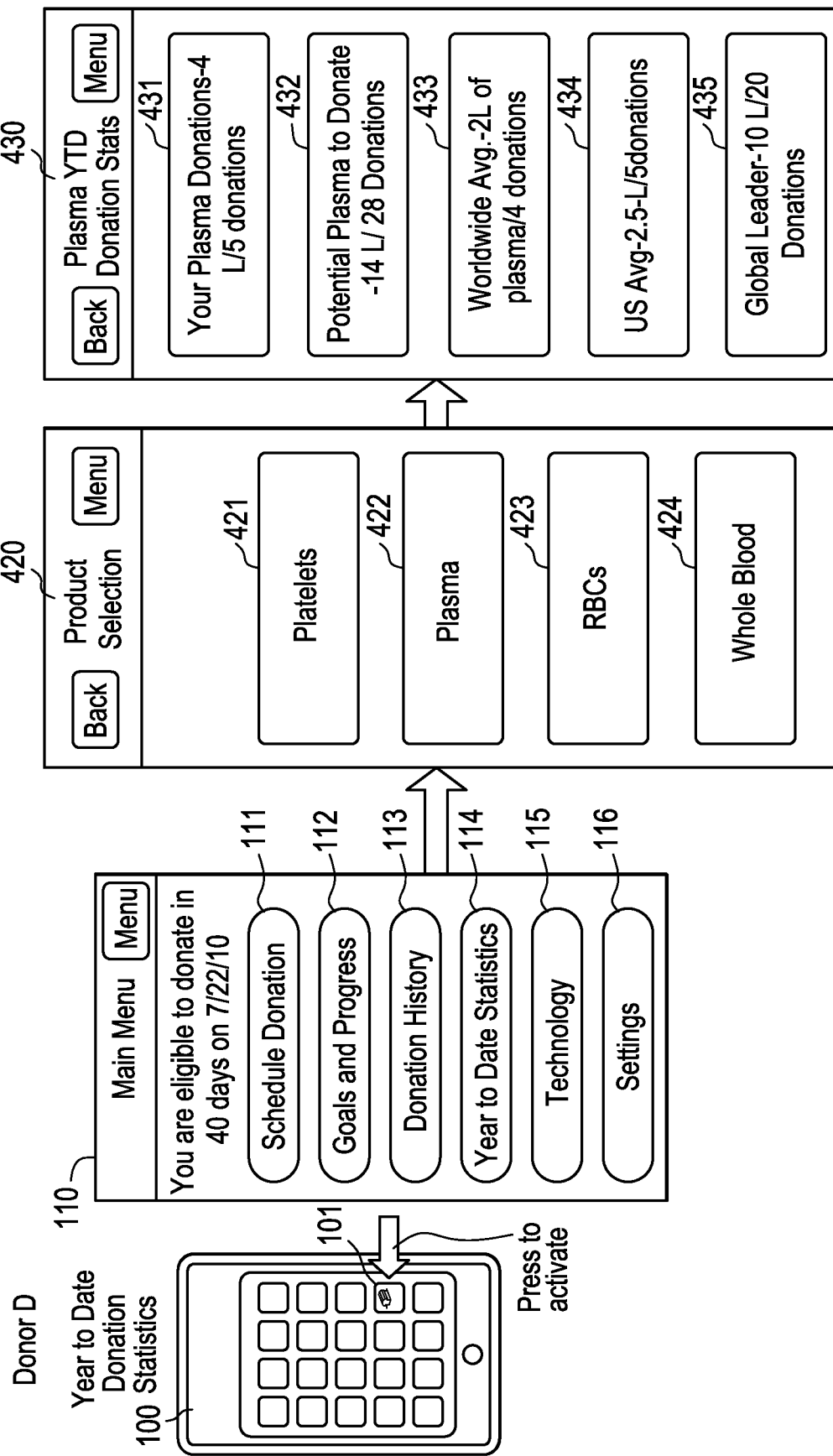

FIG. 4 shows an example product selection interface 420 to access year to date donation statistics based on selection of that option 113 via the main menu 110. The product selection view 420 provides a selectable list of blood products, such as platelets 421, plasma 422, red blood cells 423, and whole blood 424. Selecting a product, such as plasma 422, provides a view of year-to-date donation statistics 430 for the selected blood component. As illustrated in the example plasma year-to-date donation statistics screen 430 provides an indication of the user's donations 431 (e.g., 4 liters of plasma donated over 8 donations in the year-to-date). An indication of potential plasma yet to be donated for the year 432 (e.g., the user can potentially donate up to 14 liters over the course of 28 donations) can also be displayed via the view 430. Additionally, one or more averages 433, 434 can be provided. For example, a worldwide average 433 of 2 liters of plasma over 4 donations can be provided, as well as a regional (e.g., country or state-based) average 343 of 2.5 liters over 5 donations in the US. The statistics view 430 can also provide information regarding a donation leader, such as a global leader 435 (e.g., 10 liters over 20 donations).

Thus, the user selects the product/donation type for which he or she is interested in viewing statistics. The screen 430 provides information related to the amount the user has donated 431, the amount the user has donated 432, how much additional product the user could potentially donation 433, the average year-to-date donation for world 433 and region 434, and the top donor in that category 435, for example.

Figure 5:
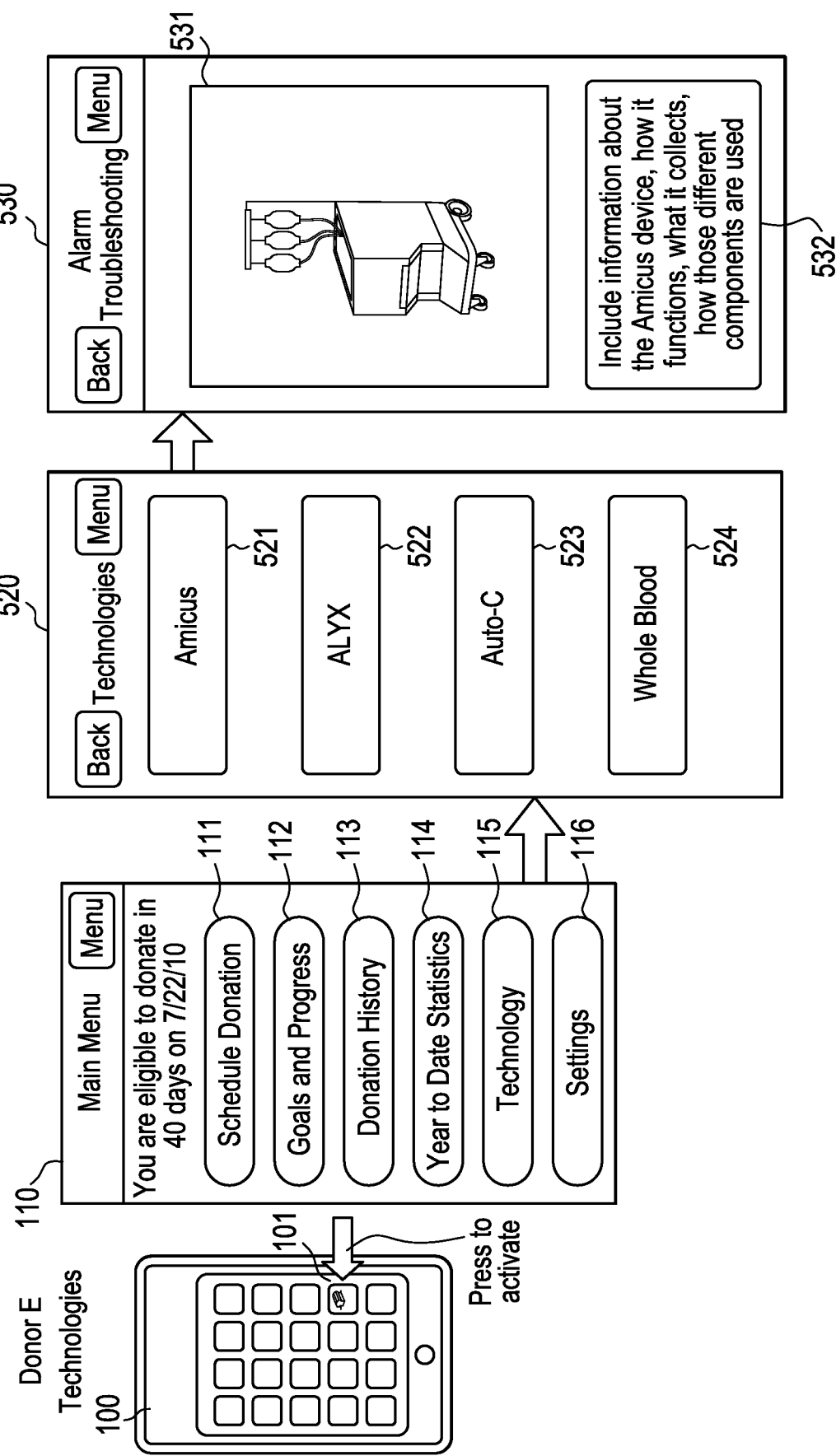

FIG. 5 illustrates an example selection of the technology option 115 from the menu 110. A technologies interface 520 includes a set of available devices or technologies available for blood product collection. Using the technologies screen 520, the user can access information about the different devices. The technologies view 520 can be used as a tool to promote automation and to educate donors regarding the different technologies to encourage donations and to ease fear or confusion about different procedure types.

For example, the technologies 520 can include one or more available technologies, such as Amicus™ separator 521, Alyx™ system 522, Autopheresis-C™ system 523, and Whole Blood 524, allowing the user to select a technology 521, 522, 523, 524 to view additional information about the selected technology. For example, selecting the Amicus™ 521 separator provides a detail view 530 including a picture 531 of the device and additional information 532 about the device, how it functions, what it collects, how the collected component(s) are used, etc.

Figure 6:
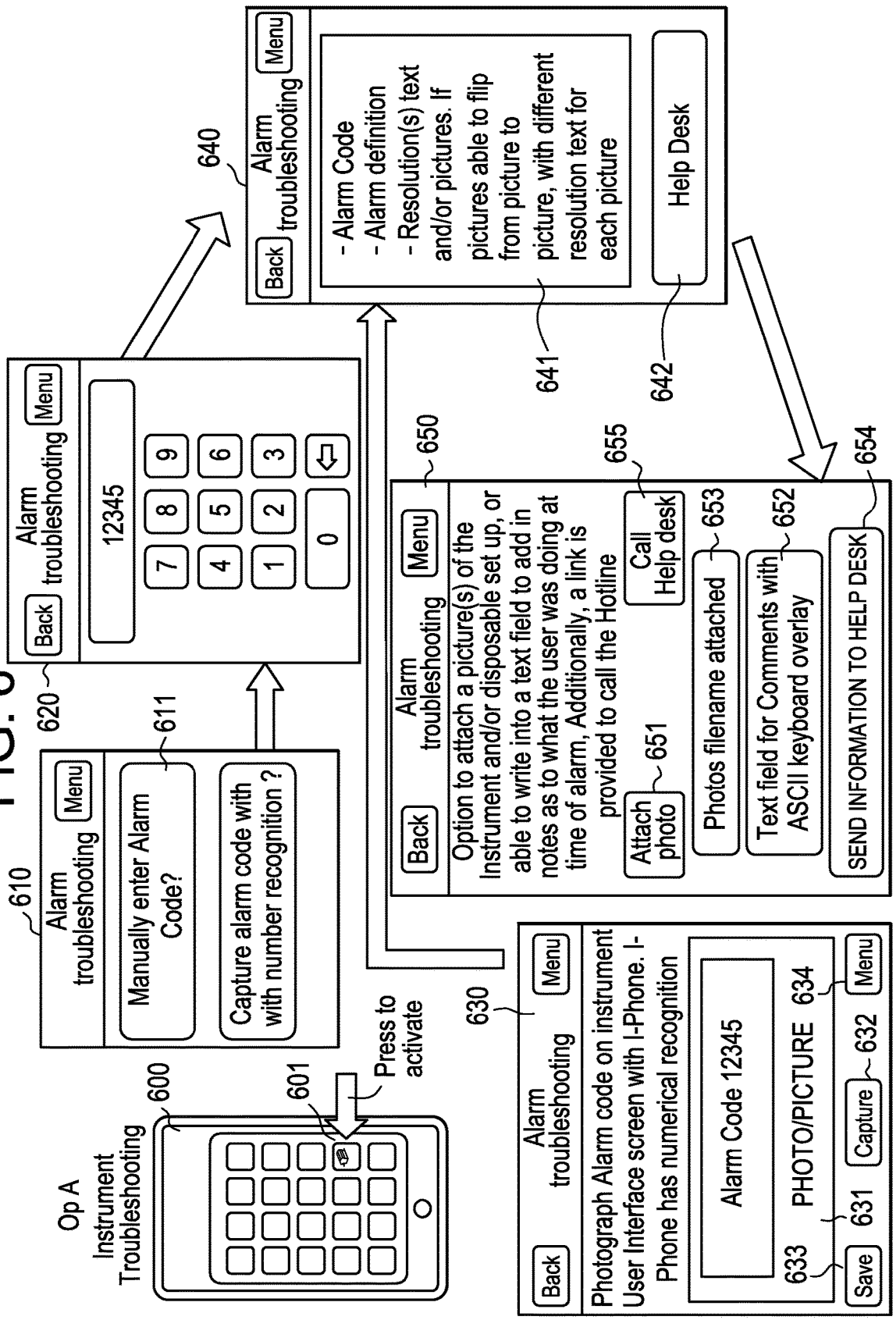
FIGS. 6-8 show example interfaces for blood collection device operators.
Figure 7:
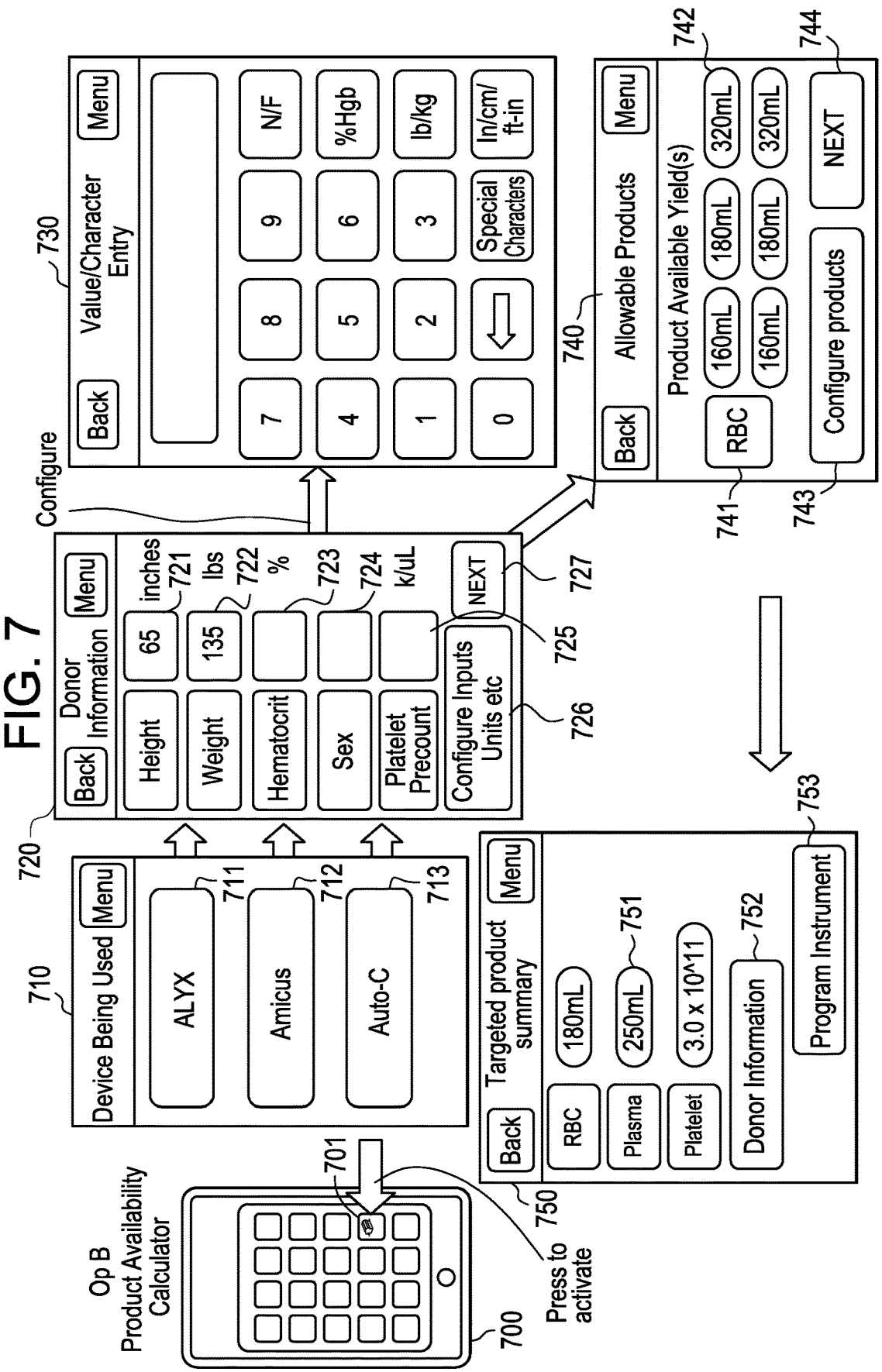
Figure 8:
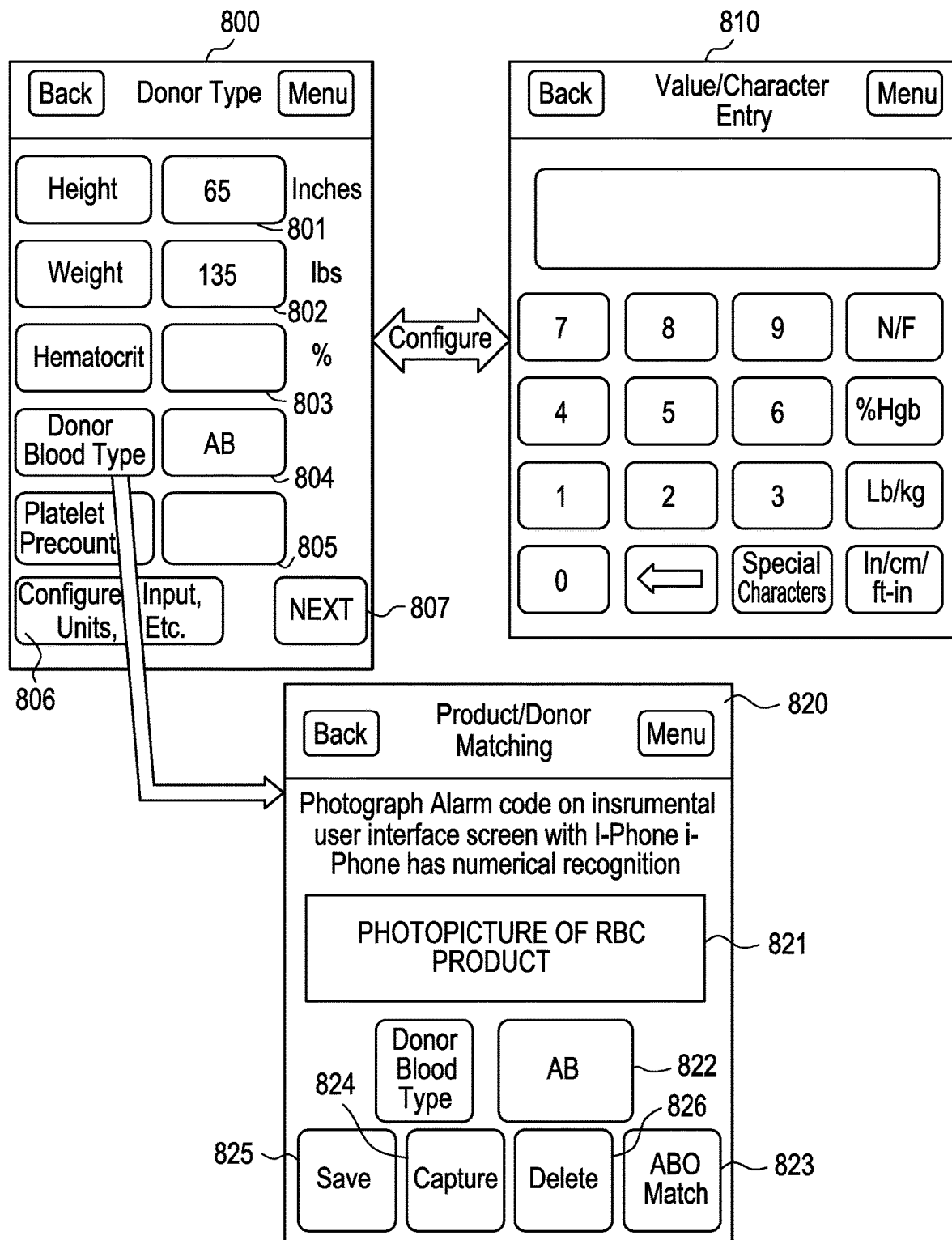

FIGS. 6-8 show example interfaces for blood collection device operators (e.g., with respect to Operators A-C). For an operator, an example application can provide instrument troubleshooting. For example, the operator can enter an alarm code or take a picture of the alarm screen or kit configuration. The application can present possible solutions; provide video(s) to resolve issue(s) if needed/desired/configured; use picture recognition and help access kit setup issues and provide resolutions; link to a hotline; etc.

In certain examples, the application can provide blood products available to be collected based on donor characteristics. The application can communicate how long the collection would take and the number of people helped based on the collection, for example. The application can allow for the transfer of procedure information and log files from an instrument using a communication protocol/medium such as Wi-Fi™, Bluetooth™, etc. In certain examples, the application can trigger/push instrument alarms or procedure information to an operator (e.g., receive a text message when an alarm occurs and provide links to troubleshooting if needed/desired/configured). The application can provide a real time scorecard (e.g., a goal was to collect 15 units with an average turnaround time of 55 minutes). The application can keep track of progress and report it back to an Administrator, for example. An operator can also see a "scoreboard" on how the operators/teams are doing, e.g. team competitions. The application can enable the operator to photograph a label on a product bag and check to help ensure that the bag and donor are correct and that the correct blood type was labeled.

As shown, for example, in FIG. 6, a computing device 600, such as a smartphone or other computer, can provide an operator application 601. The application 601 can include an alarm troubleshooting interface 610 to assist a device operator in troubleshooting an alarm or error triggered at a blood collection device, for example. The alarm troubleshooter 610 can provide the operator with an option to enter an alarm code 611, such as via a keypad 620. The alarm troubleshooter 610 can also provide the operator with an option to capture an alarm code with number recognition 612, such as via a capture screen 630. The capture screen 630 shown in the example of FIG. 6 allows a user to capture, such as using a phone and/or other camera device, an alarm code shown on a collection device 631. Via the capture interface 630, the user can capture 632, save 633, and/or delete 634 a captured image with code 631.

Following input of an alarm code, either through manual entry or photo capture, an alarm troubleshooting guide 640 is displayed. The troubleshooting guide 640 provides information 641 including an alarm definition for the alarm code along with materials to help the user resolve the alarm. For example, text and/or images to assist the operator in resolving the device alarm can be provided via the interface 640. The operator can use the interface 640 to flip between a series of pictures/images along with supporting resolution text for each picture to resolve the alarm, for example. A help desk option 642 can be provided to assist the operator in resolving the alarm, for example.

Selecting the help desk option 642 brings the operator to a help desk screen 650. The help desk screen 650 provides the user with an opportunity to attach a photograph 651 of an instrument and/or disposable set up at issue. The user can also provide information via a text field 652 regarding the problem. A listing of photos and/or files attached 653 can be provided for user confirmation, and the user can submit 654 the information to the help desk. Additionally, an option can be provided for the user to call the help desk 655.

FIG. 7 depicts an example mobile device 700 including an administration application 701 for facility and/or medical device administrators. The application 701 provides a toolbox 710 including a dashboard 711, goals 712, inventory 713, etc. Selecting the dashboard 711, for example, provides a dashboard view 720, including one or more instruments in use, such as an ALYX™ system 721, AMICUS™ separator 722, and AUTOPHERESIS-C™ system 723 (and/or an OPTIMA™ pump, a PILOT™ pump, an AGILIA™ pump, and/or other drug delivery system).

Donor values 721-725 can be color-coded, for example, for easy identification of their status. For example, green indicates that a parameter value has been entered. Yellow indicates that a parameter value has not been entered but is required, for example. Blue indicates that a parameter value has not been entered but is optional, for example. A value 721-725 can be selected to display a keypad 730, for example, to enter the parameter value. In certain examples, the keypad 730 can only show allowable values and/or other options for a given parameter 721-725. Additionally, an option 726 can be provided to configure one or more inputs, units, etc., associated with the donor values 721-725.

Selecting a next option 727 provides a list of allowable blood products 740 based on the donor parameter values 721-725. For example, based on entered and/or retrieved donor parameter values 721-725, a red blood cell product can be made available 741, along with one or more available yields 742. One or more products can be made automatically and configured 743 based on a selected instrument, for example.

Selecting next 744 presents a targeted product summary 750 including one or more blood products 751 and associated amounts, for example. Donor information 752 can again be accessed, for example. An instrument can be programmed 753 based on the donor and product information, for example.

FIG. 8 illustrates an example donor type configuration interface 800. The screen 800 includes a plurality of donor parameters, such as height 801, weight 802, hematocrit 803, donor blood type 804, platelet precount 805, etc. Values 801-805 can be entered using a keypad 810, for example. A configuration option 806 for inputs, units, etc., can be provided. A user can also access a product/donor matching interface 820. Using the matching interface 820, an operator can photograph a label on a product bag, for example, and the label is checked to help ensure that the bag and donor are correct and that the correct blood type was labeled.

As shown in the donor/product matching screen 820, a picture of a red blood cell bag label 821 is provided along with a donor blood type 822. When ABO match 823 is selected, the system either accepts the match or indicates that an ABO match has not been found (e.g., via flash, sound, message, etc.). The interface 820 allows an image to be captured 824, saved 825, deleted 826, etc.

Figure 9:
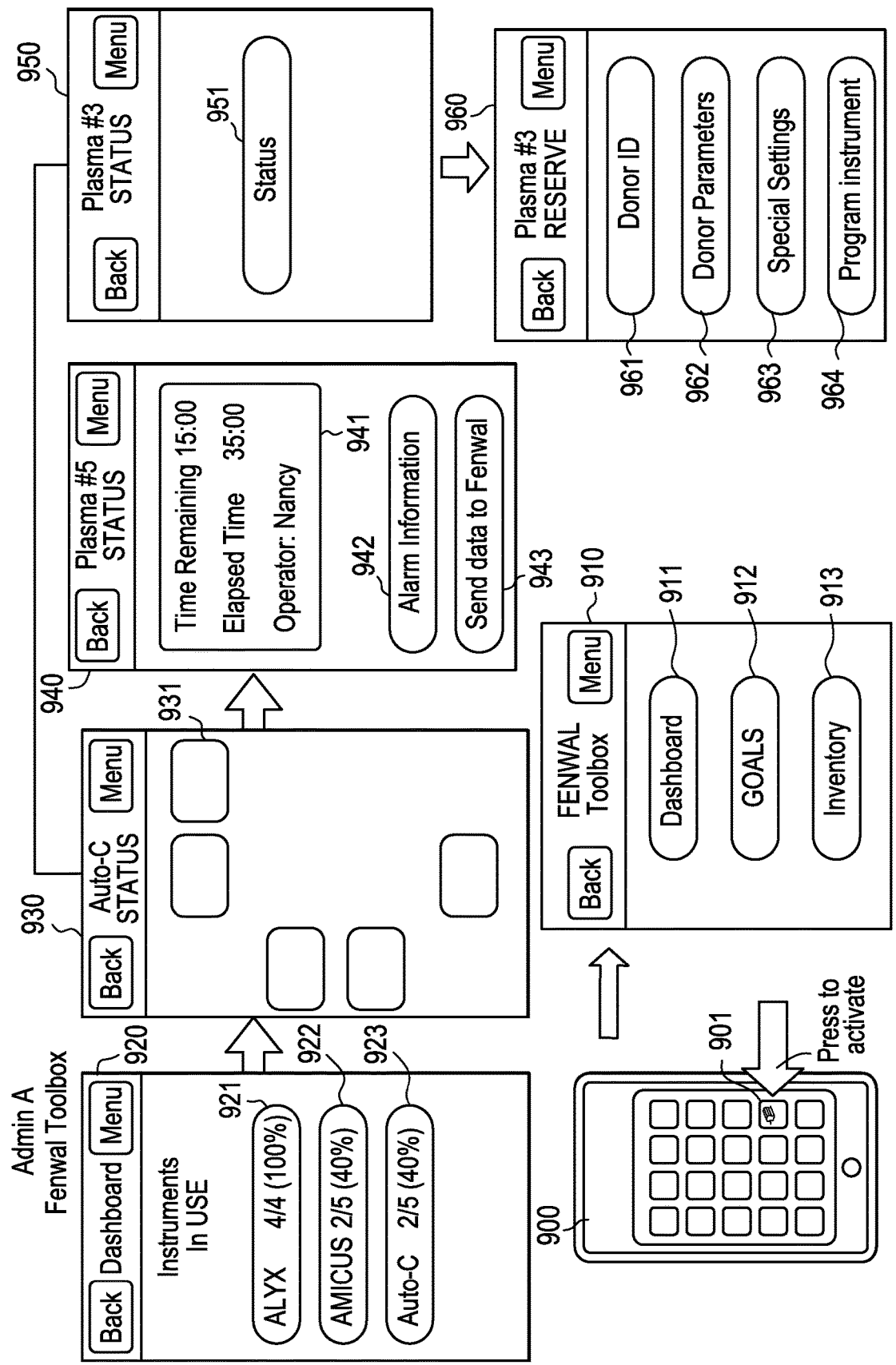
FIGS. 9-11 illustrate example interfaces for blood center administrators.
Figure 10:
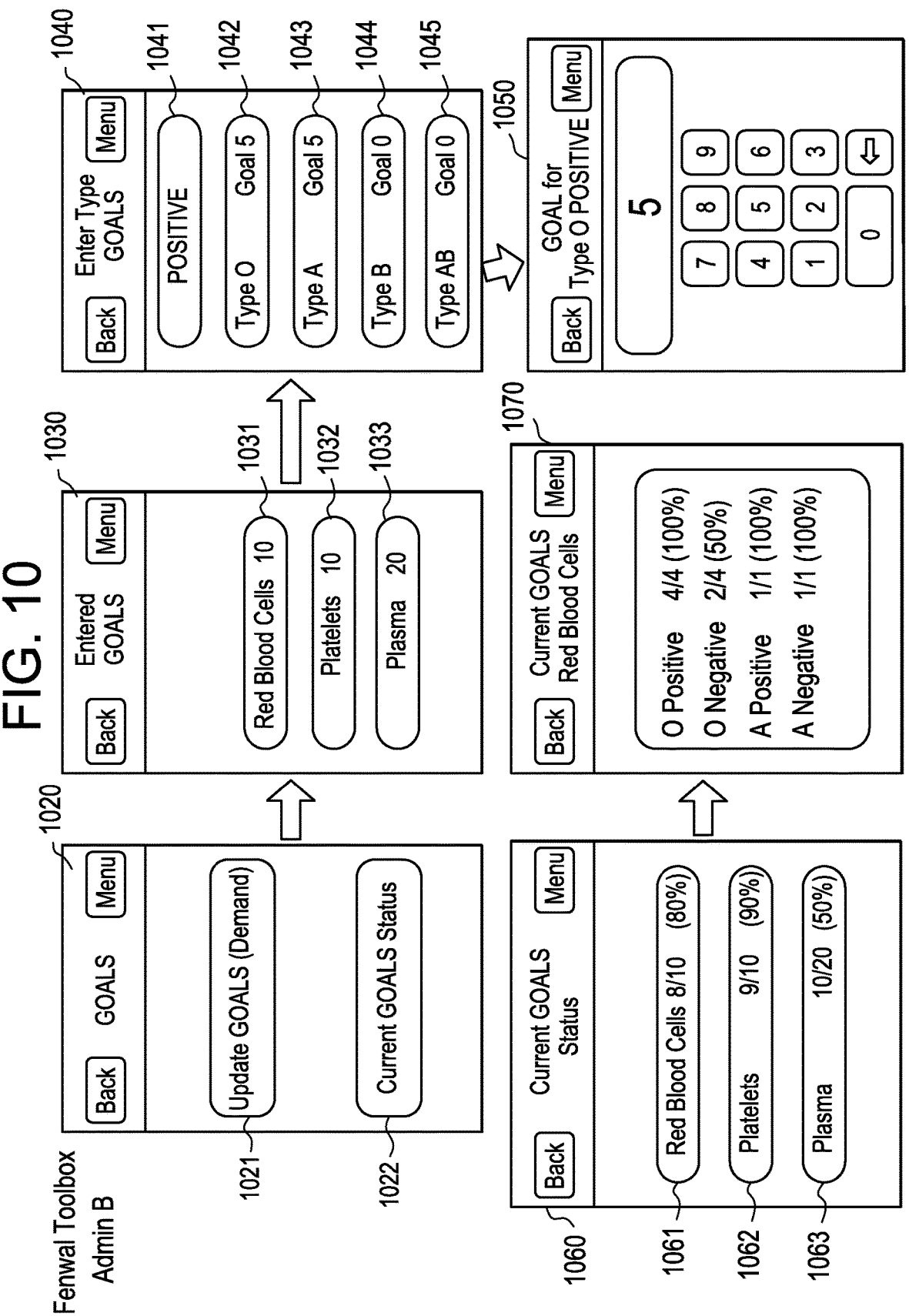
Figure 11:
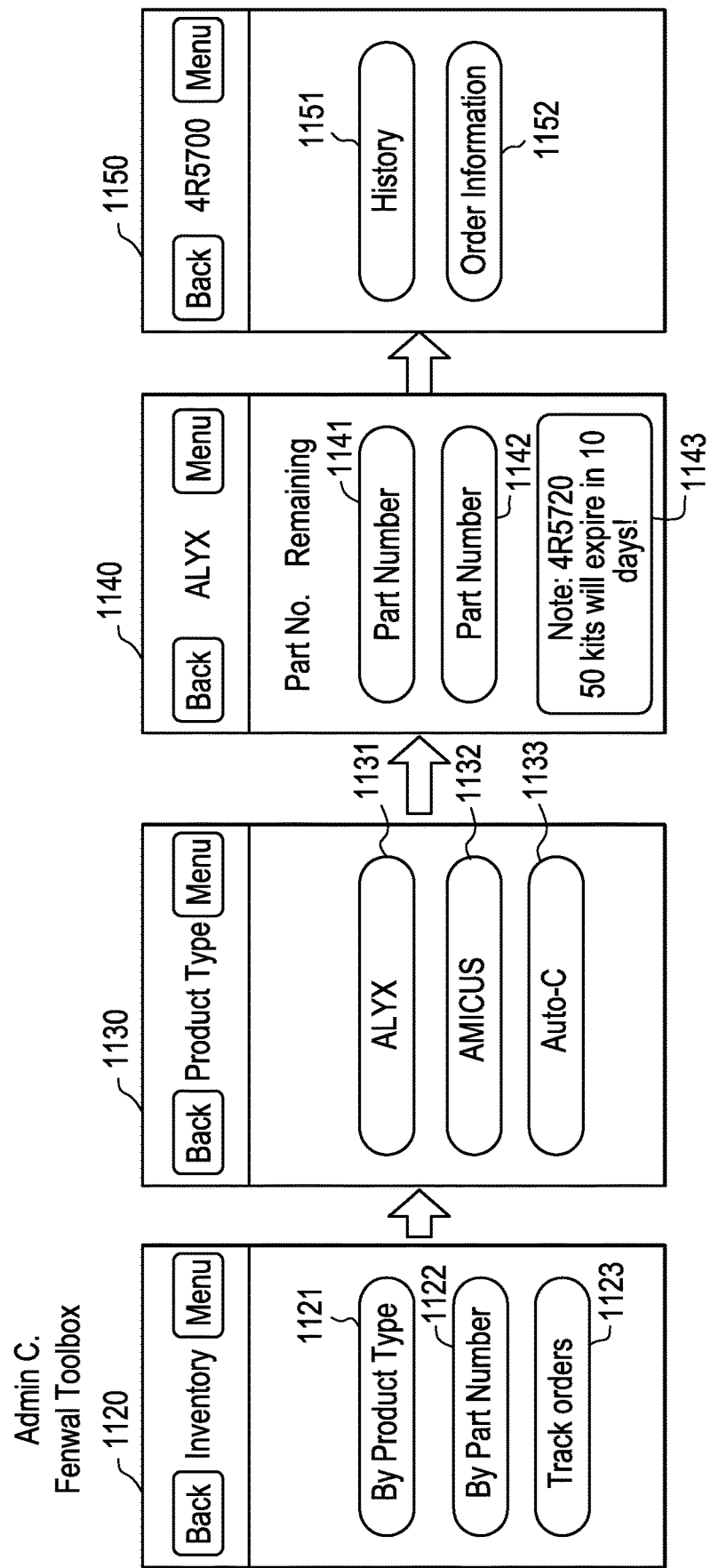

FIGS. 9-11 illustrate example interfaces for blood center administrators (e.g., with respect to Administrators A-C). For an administrator, an example application can provide a booking/scheduling tool; blood types needed, demand, available timing for instruments, etc. The application can push announcements from the administrator to donors and/or operators regarding upcoming events and/or desired for donation/collection. The application can be used to submit complaints or issues experienced using simple forms with an ability to submit photos of issues.

FIG. 9 depicts an example mobile device 900 including an administration application 901 for blood center and/or collection device administrators. The application 901 provides a toolbox 910 including a dashboard 911, goals 912, inventory 913, etc. Selecting the dashboard 911, for example, provides a dashboard view 920, including one or more instruments in use, such as an Alyx™ system 921, Amicus™ separator 922, and Autopheresis-C™ system 923.

Selecting an instrument, such as the Autopheresis-C™ system 923, provides a status view 930 for the selected instrument. The status view 930 includes a layout 931 of one or more instruments at a facility, for example. The screen layout 931 can match a room layout, for example. One or more colors and/or other indicators can be used to determine instrument status (e.g., in-use, available, instrument alarm, etc.).

Selecting a particular instrument from the layout 931 provides more detailed status information 940 for that device. The device status (e.g., Autopheresis-C™ Plasma

5) provides additional information 941 regarding a procedure being executed at the selected device, such as time remaining, elapsed time, operator, etc. Additional information regarding the procedure can be displayed, such as a product volume collected graph, etc. Information on one or more active alarms 942 for the device can also be provided, for example. Information can be sent to Fenwal 943, for example.

Instrument interface 950 depicts another example device interface for a device (e.g., Autopheresis-C™ Plasma #3) that provides a status 951 of available. A user can select the status 951 to reserve and program the device via the interface 960. Via the example reservation interface 960, the user can specify a donor identifier 961, donor parameters 962, special settings 963, etc., to provide a program to the instrument 964.

Using the administrator toolbox 910, the user can also select goals 912 to access a goals screen 1020, as illustrated in the example of FIG. 10. The goals 1020 provide user options to update goals 1021 and/or view current goals status 1022, for example. To update goals 1021, the user is provided with a goal entry interface 1030, which lists goals for one or more blood products, such as red blood cells 1031, platelets 1032, plasma 1033, etc. A user can select a blood product 1031-1033, such as platelets 1032, and then enter a blood type 1040, such as positive/negative 1041, type O 1042, type A 1043, type B 1044, and/or type AB 1045, each of which can be associated with a collection/donation goal. Each of the blood type goals for the product can be edited using a keypad 1050, for example. The user can also view current goals status 1070, including one or more products, such as red blood cells 1071, platelets 1072, plasma 1073, etc. Goals can be for a day, week, month, year, etc. Goals can be updated automatically from a data management system, such as the instrument, for example. A blood component 1071-1073 can be selected to provide current blood type goals 1070 for the selected product.

Using the administrator toolbox 910, the user can also select inventory 913 to access an inventory interface 1120, as illustrated in the example of FIG. 11. The inventory view 1120 provides a view of instruments by product type 1121, part number 1122, etc., and/or track orders 1123. Selecting product type 1121, for example, provides a product type listing 1130, including, for example, Alyx™ system 1131, AMICUS™ separator 1132, Autopheresis-C™ system 1133, etc. Selecting a product type, such as Alyx™ system 1131, provides a detail view 1140 for the selected product, including one or more part numbers 1141, 1142 along with a number of kits remaining. A note, alert or reminder 1143 can be provided, such as a note reminding the administrator that 50 kits for a part number will expire in 10 days. The user can select a part number 1141, 1142 to view additional information regarding that part 1150. From the part view 1150, the user can review a history 1151, order information 1152, etc. for the part.

Certain examples provide a dashboard application that can provide status of instrument(s) on the floor, alarms, donation status, time remaining, instrument turns, idle time, etc. A dashboard can also provide for the end of the day summaries. The dashboard can provide an ability to forward this information to a provider (e.g., Fenwal) if servicing is needed/desired/due.

An application can push donor information to an instrument to pre-program the instrument with donor preferences (e.g., smaller veins so the application sets the instrument at a slower flow ratio). The application can be configurable by a blood center and can enable blood centers to compete in a bracket-type contest for donations. The application can push thank you notes and availability of next donations to donors. The application can push reminders and/or alerts regarding donation guidelines, best practices, etc., such as to alert an operator or donor that the donor has left a donation center too soon after donating, for example.

Example applications provide an inventory management tool including kits used, kits remaining, etc., and can push notices for expiry of upcoming kits; link or push notification for ordering new inventory; allow for the photographing of a barcode to recall inventory data, etc.

For a provider, certain examples can help provide operator application, service troubleshooting, issue resolution help and/or enable proactive maintenance. For sales, an application can help track customer performance and usage rates, sales trends, complaints, etc. An application can be provided for new sales training, new publications, market data trends, events, etc.

Additional Mobile Device (e.g., Phone) Applications

In certain examples, one or more applications for a mobile and/or smart phone (e.g., an iPhone™ or BlackBerry™) are provided. When downloaded, this application causes a small icon in the shape of a blood drop or some other symbol or graphical representation typically associated with donating blood to be displayed on the main screen of the phone. This icon can be located in a corner of the main screen so as not to interfere with another main screen feature, for example. However, the icon may be displayed at any location on the screen. Within the icon, text can be displayed to show the user's distance from the nearest blood collection center (as shown in, for example, FIG. 12). Alternatively or in addition, alphanumeric data and/or another visual can be provided within and/or superimposed upon the graphical representation (e.g., the blood drop) to convey information, such as donation statistics, countdown to donor eligibility, etc., via the icon without the user opening/executing the application, for example. Further information and/or functionality can then be provided through execution of the application associated with the graphical representation on the mobile device.

Figure 12:
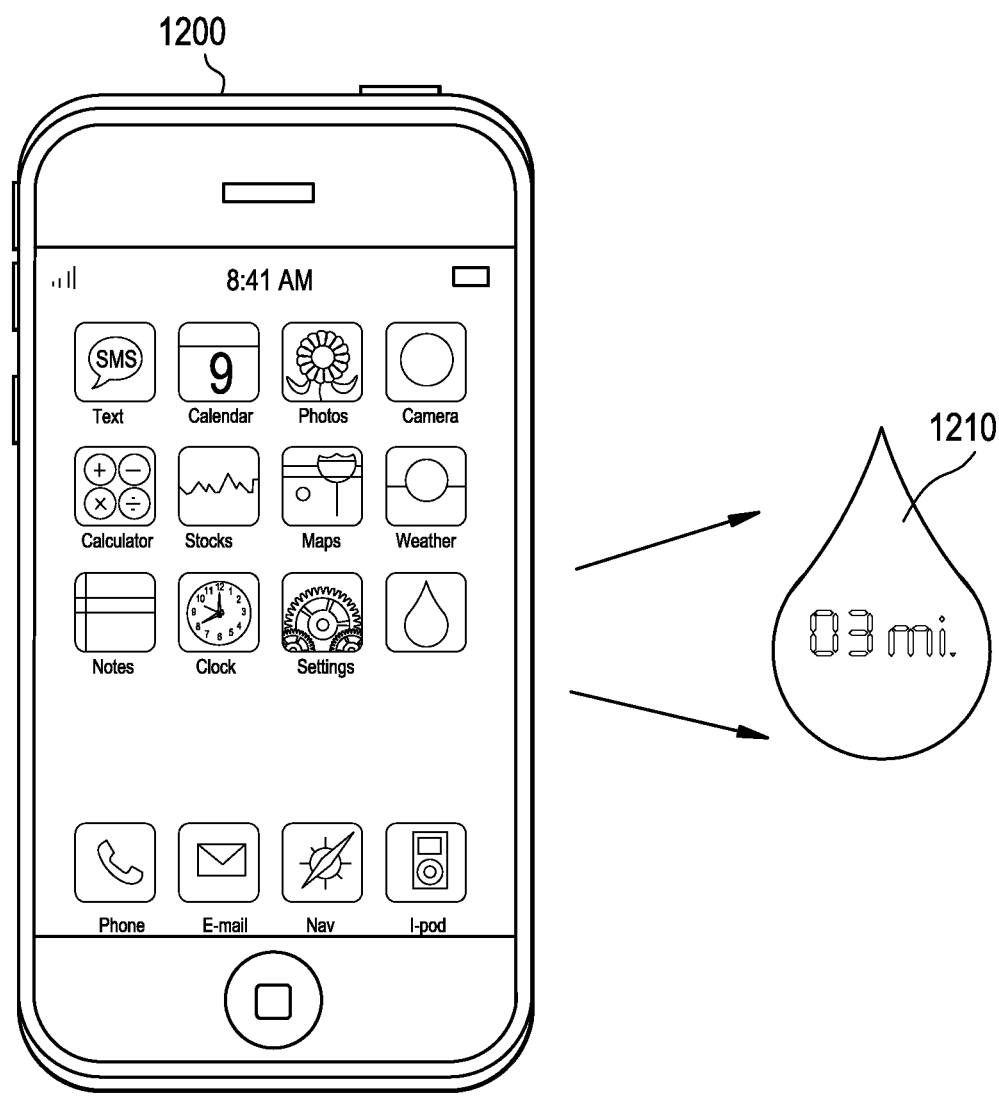
FIG. 12 illustrates an example mobile device including a donor application showing a user's distance from a blood donation center.

FIG. 12 illustrates an example mobile device 1200 including a donor application 1210 showing a user's distance (e.g., three miles) from a blood donation center. The example application 1210 is represented by a blood drop graphic in FIG. 12.

Figure 13:
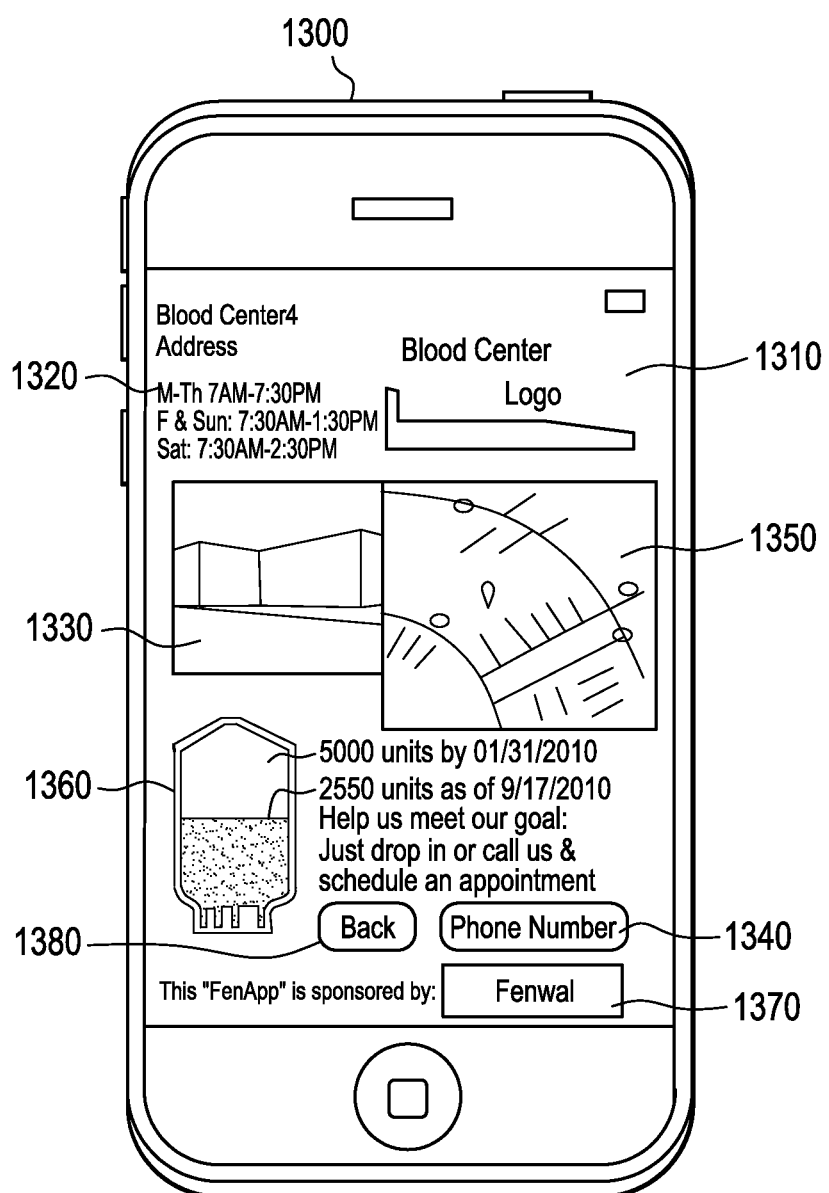
FIG. 13 shows an example information screen for a donor application.

When the blood drop icon is touched, an information screen may be displayed, such as the example screen of FIG. 13. In some examples, the information may be associated with a fixed collection center that is closest to the user. When displaying this information screen, the phone can vibrate and/or emit a sound corresponding to that of a heartbeat for a short amount of time. This screen can include the nearest blood collection center's: a.) corporate logo or symbol 1310, b.) address 1320, c.) building or profile picture 1330, d.) phone number 1340, e.) a snippet of a Google™ (or other equivalent) map showing the blood collection center's location on the map 1350, f.) an icon in the shape of a blood bag showing the nearest blood collection center's current monthly collection total, as well as its target monthly collection goal 1360, g.) a small provider (e.g., Fenwal) logo 1370, and/or h.) a back button 1380, for example.

A more detailed description of some of the items on the information screen is provided. For example, when the phone number (d) is touched, the phone can automatically call the nearest blood collection center's recruitment or scheduling department. In this manner, the phone user is enabled to schedule an appointment to donate blood if he or she so chooses. When the phone conversation is ended, the user can be brought back to the phone's main screen.

Figure 14:
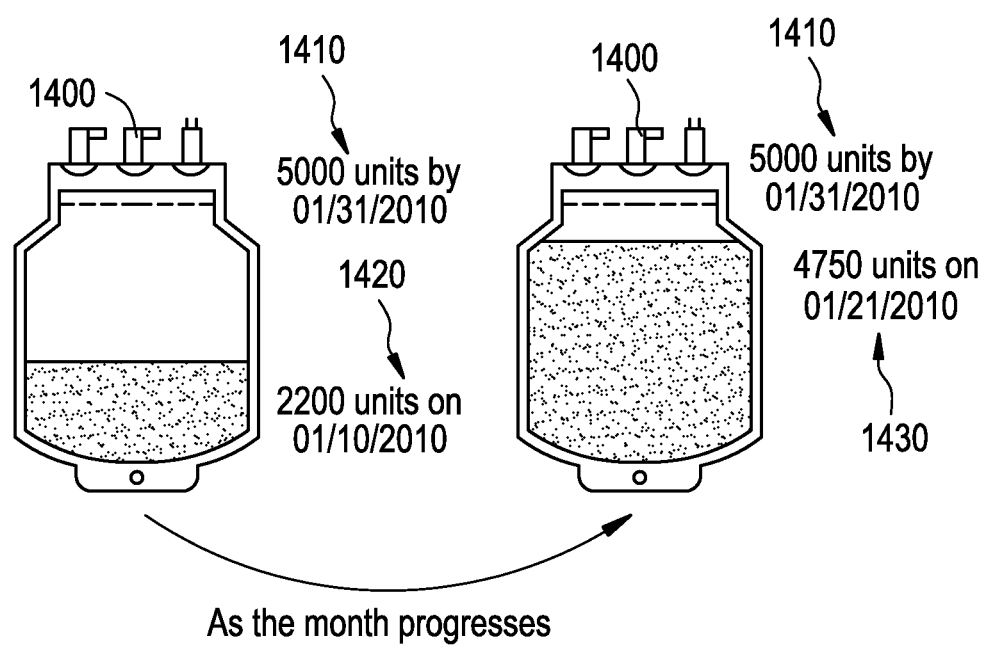
FIG. 14 illustrates an example graphic showing visual progress as a collection total approaches a target collection goal.

The blood bag icon (f) displays a nearest blood collection center's current monthly collection total as well as its target monthly collection goal, for example. This data can be made available to the application using the phone's built in Internet and/or other network capabilities to access a registration website. As illustrated, for example, in FIG. 14, a blood bag 1400 would "fill up" as the current monthly collection total approaches the target monthly collection goal. A goal 1410 can be provided with respect to the bag or other graphic 1400, such as a goal of 5000 units by Jan. 31, 2010. A current status 1420 can indicate, for example, that 2200 units have been collected as of Nov. 10, 2010. As the month progresses, the graphic 1400 can indicate progress 1430 toward the goal 1410 (e.g., 4750 units as of Jan. 21, 2010).

In this way, the user quickly determines how significant the nearest blood collection center's current need for blood may be. In some examples, the date that the data was last updated may also be displayed. In some examples, the blood bag icon may be an optional feature. For example, when a blood bank center registers, it may select not to display the blood bag icon and, thus, the center would then not have to update the data regarding its current monthly collection total and/or the target monthly collection goal. If a center decides to include the blood bag icon, data may be input by the center to keep the data up to date. For example, the registered blood collection center may update the current monthly collection total and/or the target monthly collection goal on a daily basis. In some examples, the data may be entered using the same website as used to register the collection center. In some examples, the center may register on-line. In some examples, when registering, the center may upload and/or provide their address, corporate icon and/or a picture of the building where it is located.

In some examples, the blood drop icon on the main screen provides the user with an unobtrusive but constant reminder of the need to donate blood. Rather than utilizing potentially annoying phone calls asking the donor to come back again and donate, blood centers participating application project and/or utilizing the examples descried herein will now have a means of continuously reaching out to their donor base via registry of their blood collection centers on the registration website. The application enables 24 hours a day, 7 days a week passive recruitment that is not disturbing to the donor.

In some examples, once an application is installed, it continuously, but in the background, accesses the registration website using a phone's (e.g., an iPhone™ or other smart phone) built in Internet and/or other network capabilities and calculates the user's distance from each blood collection center in each account by retrieving the street addresses stored in the registration website and then providing these addresses to the phone's built in global positioning system (GPS) and/or other location function. The GPS function then calculates the user's distance from each registered blood collection center and/or may provide corresponding route information upon selection, for example. In some examples, the application interacts with public-access map tools such as, for example, MSN™ Maps, Google™ Maps, etc., and then, once received, the application may display the distance that the user is from the blood collection center. In some examples, the application enables the user to select which of the public-access map tools are utilized.

In some examples, after the user's distance from each registered blood collection center is determined by a phone's GPS function, the application may automatically select the closest blood collection center and display the distance of the blood collection center from the user (e.g., in miles) within the blood drop icon on the main screen. In some examples, the user can select one of the blood collection centers they wish to go to and appropriate directions to the selected blood collection center may then be retrieved and then displayed.

When the map snippet (e) is touched, it can automatically activate the phone's built in global positioning system (GPS) and/or other geolocation/terrestrial location function and begin providing the user directions from his or her current location to the location of the nearest blood collection center, for example. A back button can be incorporated to enable the user to navigate back and forth from the GPS tool to the information screen.

In some examples, when the blood drop icon is pressed, the application grabs the data associated with the closest blood collection center, again by accessing the registration website using the a phone's, e.g., an iPhone™, built in Internet capabilities, and uses this data to populate the fields that are displayed on the information screen, including, for example, a.) the center's corporate logo or symbol, b.) the center's street address, c.) a building or profile picture of the center, and d.) the center's phone number, and/or e.) a snippet of a Google (or other equivalent) map showing the center's location on the map, and, if the optional monthly data feature is enabled, f.) the center's current monthly collection total and/or the center's target monthly collection goal (both of which are used by the blood bag icon ((f), as previously described).

In some examples, because, in the background, the application may continuously be accessing and analyzing the blood collection center data stored on the registration website, as the user moves about, his or her distance from the various registered blood collection centers changes. Correspondingly, the data displayed in the blood drop icon on the main screen and the data displayed on the information screen may vary and/or change according to which blood collection center a phone user happens to be closest to at any given time.

In some examples, the blood drop icon on the main screen tells the user how close he or she is to a blood collection center. Notifying users of the nearest blood collection center may notify users of (e.g., enable the discovery of) blood collection centers of which he or she was previously unaware.

In some examples, the information screen may attempt to motivate the user to donate by providing them with information to locate and contact a blood collection center and/or by communicating to the user the center's current need for blood in terms of the center's monthly goals.

In certain examples, when the provider logo (g) is touched, the phone's built in Internet and/or other network capabilities can be used to bring up a provider's (e.g., Fenwal's) external website.

When the back button (b) is touched, the user can be brought to the phone's main screen, for example. Alternatively and/or in addition, after a certain amount of inactivity while on the information screen, the application can automatically return the user to the main screen.

In certain examples, a user can register the application via a registration website, accessible over the Internet, an intranet, a virtual private network, etc. The website can be a password protected part of or extension to a provider's (e.g., Fenwal's) external website, and the website can be periodically supported by the same group of people who already support the external website. An application may retrieve data from the registration website and display the data. In certain examples, an application may involve the creation, and periodic support, of the registration website.

The registration website can include a number of blood center accounts and can be used in a variety of ways, including the following examples.

In some examples, participating blood centers may be provided with a unique username and password for access into their specific account within the registration website.

In some examples, when logged into their account on the registration website, the blood center can register by providing: a.) a street address (possibly including hours of operation), b.) a phone number, and c.) a profile picture for each blood collection center that the blood center wishes to register into the application. The profile picture can be any image of the blood center's choosing, but it is envisioned that it might be a picture of the building corresponding to the registered blood collection center. Also, the blood center can provide an image of its corporate logo or symbol.

In certain examples, a mobile collection site can be registered as well by providing a.) a street address, b.) a phone number, and c.) a profile picture, as well as by toggling a switch on the website that, when toggled, requires the blood center to also enter a date (e.g., mm/dd/yy) and a time range (e.g., two specific times between 12:00 AM and 12:00 PM). In this fashion, the application can factor the registered mobile collection site into its nearest blood collection center calculation on the specific day and time provided. In some examples, there may be a limit placed on the length of time (e.g., one day) that the mobile site may be displayed and/or be operating for to ensure that mobile sites that are no longer operating are not inadvertently displayed.

In some examples, a blood center can choose whether or not to enable the optional monthly data feature of the application. In the blood center's account on the registration website, the feature can be default set to "off," but, if toggled "on," it enables the center to also fill in a current monthly collection total and a target monthly collection goal for each of their registered blood collection centers, for example.

In certain examples, the current monthly collection total can be a number representing the blood collection center's current number of whole blood units collected for the month so far. A current monthly collection total can be provided for each of the blood collection centers registered. The participating center may assign a responsible person from each of their blood collection centers with the task of updating their respective center's current monthly collection total at an appropriate interval of their choosing (such as daily or weekly). Also, when this number is input or updated, the registration website can automatically update, set, and/or display the date that the current monthly collection total was entered or changed.

In certain examples, the target monthly collection goal can be a number representing the blood collection center's total monthly whole blood collection goal in terms of units collected. A target monthly collection goal can be provided for each of the blood collection centers registered. Again, when this number is input or updated, the registration website can automatically update, set, and/or display the date for achieving this goal as equal to the last day of the current calendar month.

Thus, if the blood center wishes to support the optional monthly data feature, they can use their username and password to log in to their account on the registration website and update or change their target monthly collection goal(s) and current monthly collection total(s) as appropriate. Because access into the accounts on the registration website is password protected, misuse or misrepresentation of this data is mitigated since each individual account is set up with a unique username and password.

Referring back to the blood bag icon (f), the data displayed alongside the icon is retrieved by the application using the phone's built in Internet and/or other network capabilities to access the registration website and retrieve the target monthly collection goal and the current monthly collection target for the nearest blood collection center.

In certain examples, the blood center can disable the optional monthly data feature at any time by logging into their account on the registration website and toggling the feature to "off." If the feature is toggled "off," when the application attempts to retrieve the target monthly collection goal and the current monthly collection target for the nearest blood collection center, it will recognize that the feature is toggled "off" and will, accordingly, cease displaying the blood bag icon (f) until it recognizes that the feature has been turned "on" again.

Promotional materials may be used to explain the application project and can provide directions for downloading the application onto a phone, and they can also explain how to use the application itself. These materials can be handed out by the blood center to their donors after they donate. In this way, the blood center can use the application as an incentive and reward program for their donors. For example, these promotional materials can include a one-time use download code, which can be entered by the donor prior to downloading the application onto a phone.

In some examples, an application can be used in conjunction with promotional material by blood collection centers to incentivize their donors and reward them after donation. For example, the application constantly travels with a phone, and the phone may constantly travel with the donor (e.g., all day, every day). Ways for blood collection centers to reach out to donors after they donate are to: follow up and call them, email them, or send them postal mail. These approaches involve the blood collection center's time and effort. The application described herein allows centers to stay connected to the donors and the donors to stay connected to the blood centers. One-time mobile donors may be more likely to switch over to and become regular fixed site donors because the application facilitates an ability to look up contact information for fixed site locations.

In some examples, only blood centers using a provider's (e.g., Fenwal) products will have accounts on the registration website. Thus, the application can indirectly push donors back to just the blood collection centers where a particular provider's name (e.g., Fenwal) is listed. Unless the blood center opts to use the optional monthly data feature, the application, in general, doesn't require anything more than a one-time commitment from each stakeholder (e.g., when registering for the service).

In some examples, each blood center may only have to register their blood collection centers once. However, it may remain the blood center's responsibility to ensure that their blood collection centers' data stored in their account on the registration website stays accurate and up to date.

In some examples, a provider (e.g., Fenwal) may develop, but not necessarily support, the application and the registration website. In certain examples, if a blood center volunteers for but, at a later date, opts out of a participating application project entirely, a provider's information technology (IT) group (e.g., Fenwal) may delete their account from the registration website, for example.

In some examples, a provider (Fenwal) may only have to work with a blood center once to set up their account on the registration website. However, in some examples, a provider may periodically replenish the center's stock of promotional material. By displaying corporate logos and symbols, the application provides advertising for both the provider (e.g., Fenwal) and for those blood centers that choose to participate in an application project.

In some examples, the donor may only have to install the application once and is not obliged to interact with the application in any other way after its initial installation.

Figure 15:
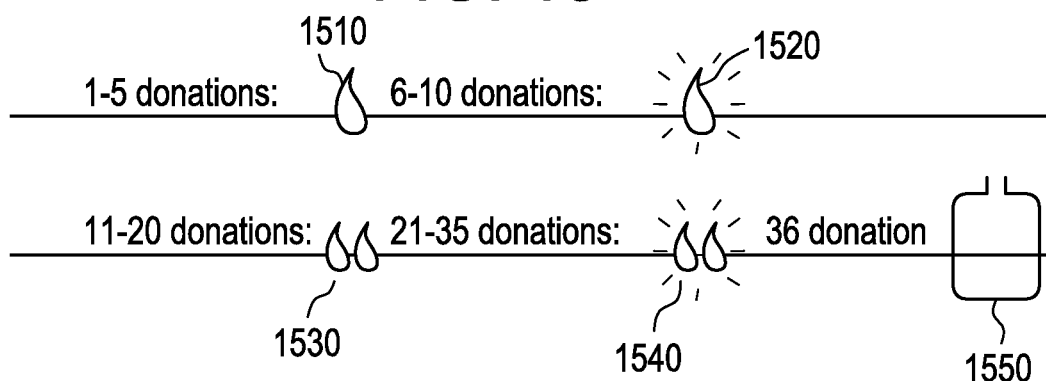
FIG. 15 depicts example donation update graphics.

In some examples, the blood center may further incentivize a donor that utilizes the application by providing him or her with a code that, when accepted by the application, keeps track of his or her number of donations. For each donation, the donor receives another code and/or password. After a specified number of donations are acquired, the blood drop icon can update (see, for example, FIG. 15). For example, a donor's blood drop icon 1410 can progressively update to a more impressive symbol 1520, 1530, 1540 as his or her number of donations increases.

In some examples, using data stored on the registration website, the application can keep track of a blood collection center's target versus actual collection amounts for each month over a one year window, etc., and, when the blood bag icon (f) is pressed, the application can display this information to the user.

Figure 16:
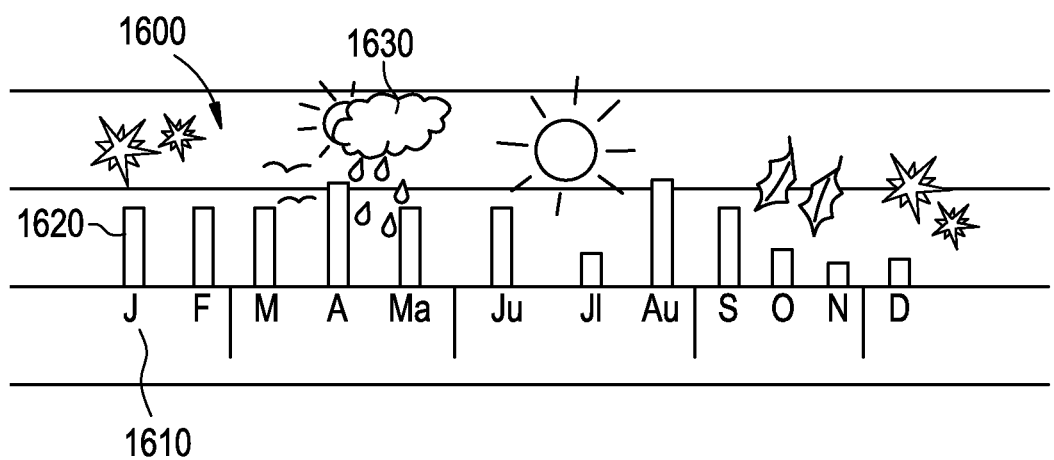
FIG. 16 depicts an example histogram that can be displayed via an information screen.

FIG. 16 depicts an example histogram 1600 that can be displayed after a user presses the icon (e.g., the blood bag icon) on the information screen. The histogram 1600 can display information to a donor such as, whether or not his or her monthly target has been met. Additionally or alternatively, the information displayed may indicate the amount over or under the monthly target amount that the donor is. In some examples, the background of the histogram may be selected by the user, be representative of the seasons (e.g., fall, winter, etc.) and/or include a corporate logo (e.g., Fenwal). Depending on the origination of the mobile device (e.g., an iPhone™, BlackBerry™, and/or other smart phone), the display of the histogram may change. In some examples, the histogram may display past targets for blood collection centers and/or the amount received for a particular and/or specified amount of time. For example, as illustrated in FIG. 16, a month 1610, monthly total 1620, and season 1630 can be displayed along a timeline for the donor.

Tracking Donated Blood

Donated blood is to be tracked and triaged. When blood is collected from a remote site, it can be difficult to communicate to the main office which unit is being collected at what time and where the unit is located at the present time. In many cases it is important for the blood center because some/many units need to be processed within an eight hour window, such as for plasma. Currently, this is being decided when the units are coming in by searching through handwritten notes that collection staff recorded at the point of collection. This process is called triaging. Until blood process staff go through entire units that are coming in, they do not know which unit is time-sensitive. Also, tracking during transit can be problematic. One can sometimes call the driver to ask the location of the van, but the driver does not always know which unit he is carrying back.

In some examples, using a phone (e.g., an iPhone™ or some other mobile device), the operator can record a DIN (donor identification number) and collection time. In some examples, using a phone or some other mobile device, the operator can record additional optional information such as gender, blood (ABO) type if known, weight of the unit, etc.

In some examples, using a phone or some other mobile device, the operator can record a "cooler number" that the unit of collected blood is going in. In some examples, using a phone or some other mobile device that is attached to, coupled to, or incorporated with the cooler, the main office can track individual unit(s). In some examples, using a phone or some other mobile device, the units are tracked as they are coming into blood center. Thus, the blood center knows which unit(s) is/are time sensitive, for example.

In some examples, using a bar-code reader application, one can recognize the product code and DIN. In some examples, an example application can automatically load the information into an e-mail system and/or data system and automatically send the e-mail or data to a main computer(s). At that time, additional information can be added as well. For example, a "cooler" can have an identifier as well. The identifier may be a bar-code or an assigned number, for example. As the operator puts the unit in the cooler, the operator can open the example application and find (e.g., scroll down) the unit he or she is working with, and add the cooler information by punching the number or bar-code scanning, for example. Another e-mail or data may be sent (and/or be combined with the email with produce code and DIN above), for example. In some examples, the cooler itself has a phone and/or other communication device (e.g., an iPhone™ and/or other smart phone) attached. Using a tracking program, an operator or user can track the phone/device that is attached to the cooler. Since the main computer knows which unit is placed in which cooler (e.g., the unit associated with the cooler when placed therein by bar-code scanning), individual units are being tracked, for example. In some examples, in a receiving dock, operator(s) have a phone with triaging information being pushed to the phone. The information includes which units have to be triaged first, for example. The operator looks for the cooler and finds the unit and processes the unit accordingly. In some examples, as the operator selects six units to process, he or she opens the example application and looks (e.g., scrolls down) for the six units and checks out the six units. The main computer knows who has the possession of those units.

Interactive Teaching Application

Figure 17:
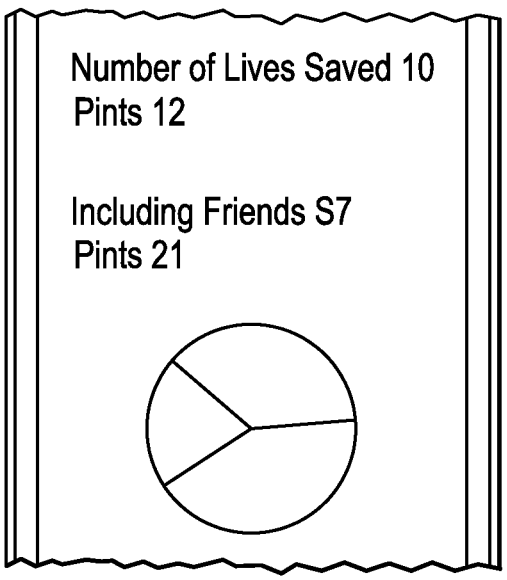
FIGS. 17-19 depict example screen shots of a mobile device running an application that increases donor awareness.
Figure 18:
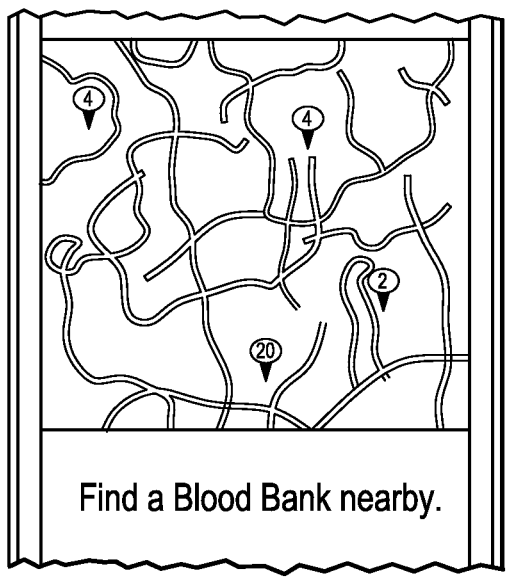
Figure 19:
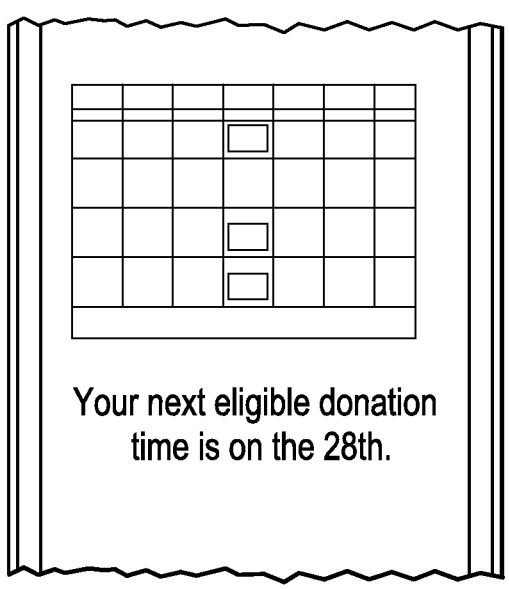
Figure 20:
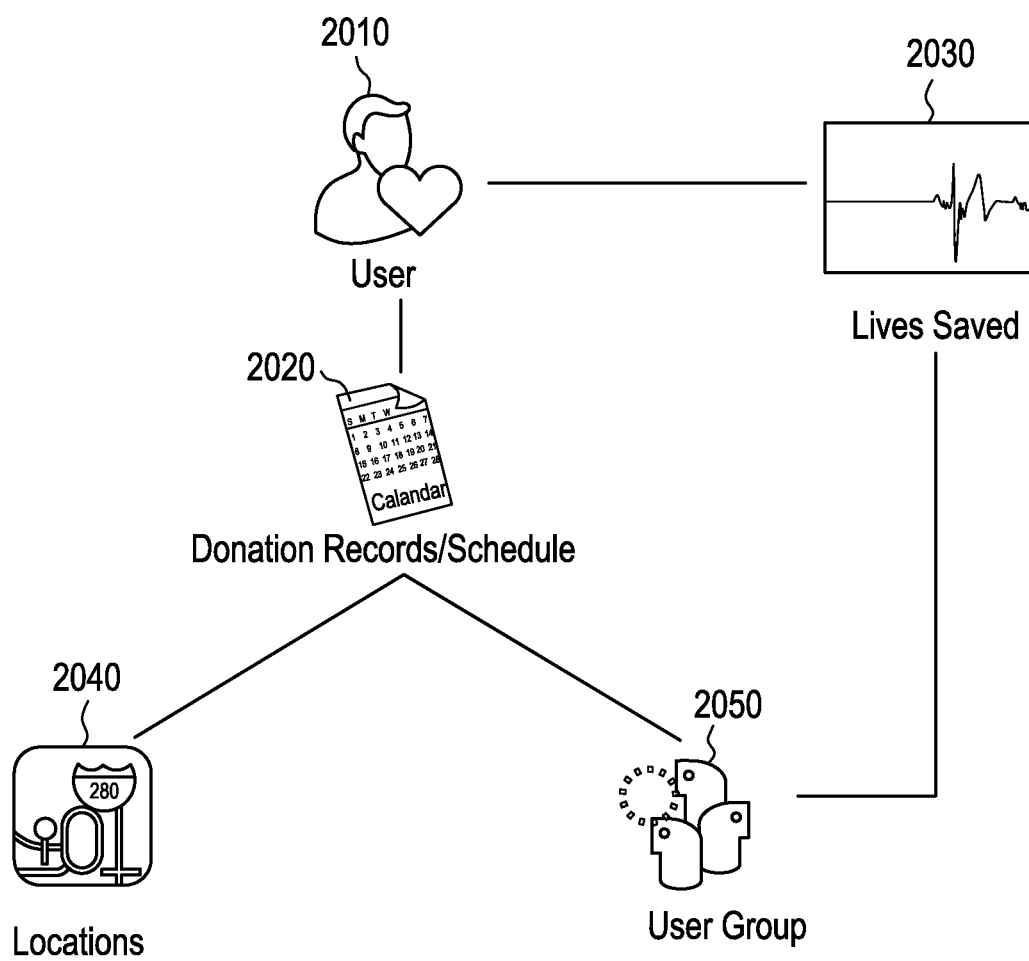
FIG. 20 depicts an example flowchart for a blood donor application.

FIGS. 17-19 depict example screen shots of a mobile device (e.g., an iPhone™, iPad™, and/or other smart phone or handheld computing device) running an application that increases blood/plasma donor awareness. FIG. 20 depicts an example flowchart for the application. For example, the application may convey information related to the number of lives saved based on the amount and/or frequency of the donor's donation(s) (as illustrated in FIG. 17, for example). In some examples, the application may convey information related to the number of lives saved based on the amount and/or frequency of donations by the donor's friends and/or family, sponsored by a provider (e.g., Fenwal) (as shown in FIG. 17, for example).

In some examples, an application may provide a convenient tool and/or applications including maps and/or directions to the nearest donation facility/facilities (as illustrated in FIG. 18, for example). In some examples, the application may provide a convenient tool and/or application(s) that includes a personalized donation schedule (e.g., the date that the donor is next eligible to give a donation, as shown in FIG. 19, for example) and access to "donation buddies" schedules (e.g., donation schedules) by encouraging users to share the applications with friends and/or family members.

In some examples, an application may be a mobile donation station application that provides a common platform for donors and/or the general public to gain an understanding of cumulative lives saved based on frequency and/or the quantity of blood/plasma donations (as depicted in FIG. 20, for example).

As shown in the example of FIG. 20, a user 2010 accesses donation records and/or schedule 2020. Using the records/schedule 2020, the user 2010 can retrieve one or more donation locations 2040, for example. The user 2010 can also access a user group 2050 for information such as an estimate of a number of lives saved 2030 by blood donations, for example.

By utilizing the applications and the examples described herein, a provider (e.g., Fenwal) utilizing a phone and/or mobile device application (e.g., an iPhone™), for example, may gain improved visibility. In some example, other institutions, blood banks, affiliates, etc. may be provided with access to a database of users that are utilizing the application.

In some examples, the application promotes donor awareness of the benefits of donating blood/plasma, etc.

In some examples, the application may provide a chart that details RBC, plasma, and/or platelet collection levels for the donor's center, the entire state, and/or the country (e.g., detailing collection levels versus need levels, etc.). In some examples, the chart may provide a visual representation of how their donation affects the overall group of donors. Such an approach of visually representing donor center levels may increase donor awareness of the need to donate and/or perhaps urge them to convince others to donate as well.

In some examples, an interactive application teaches donors about blood, the therapeutic uses of the various blood components, and/or how the automated Fenwal technologies or other provider technologies are designed to maximize the collection of platelets (e.g., on an Amicus™ separator), plasma (e.g., on an Autopheresis-C™ system) and red cells (e.g., on an Alyx™ system). This application may also include some basic information about how the automated devices function. In some examples, the application may describe how they draw the donor blood in, separate it into the various components and return the unnecessary components back to the donor. In some examples, the target audience may be the younger donor population. In some examples, the application may be given to whole blood donors during their donation to educate them about how to benefit more patients with a single donation when donating using automated technology. The application educates the donors, which may make them come back more often, and promotes a provider's (e.g., Fenwal) automated technologies.

Blood Component Loss Calculation

The examples described may include an application that enables RBC and plasma loss on an instrument such as an Amicus™ system to be calculated if they cannot re-infuse the donor. For example, the application can calculate and/or determine the answer by having a person enter if it is a single needle (SN) or double needle (DN) procedure, what the donor's hematocrit is, and/or what cycle volume they were using if it was a SN procedure.

Blood Collection Screening Application

In some examples, an application enables donor screening for automated component collections by, for example, providing a brief donor questionnaire to determine if a donor qualifies for apheresis donations based on donor sex, height, weight, blood type, CMV +/−, etc., and identify any special needs for donor's blood type or specific components, and/or provide a brief video or slideshow explaining the procedure(s) to the donor. Blood centers can enter daily collection targets to customize options.

Blood Donation Tracking, Reminders, Scheduling and/or Medical Information

In some examples, the application allows donors to make appointments at a blood center, and/or the application may enable the center(s) to remind the donors of their appointments. In some examples, the application enables scheduling systems of different blood centers to interact to facilitate scheduling of donors.

In some examples, an application enables a donation calendar that enables regular donors to track their donations and set alarms to schedule appointments when donors are eligible for their next donation. Certain examples provide an option to download donation history from blood center websites or manually enter data to track blood pressure, cholesterol, etc. Certain examples locate nearby blood centers (e.g., utilizing GPS) by referencing, for example, a Fenwal database.

In some examples, by providing an application, accessible and/or executable by phone (e.g., a smart phone such as an iPhone™), a blood center can access mobile society communication channel(s). Through such an application, a blood center can maintain near constant connection with donors to help build donor loyalty and potentially improve donor frequency. The application can connect with a blood center's existing software systems.

The application can alert donors when they are approaching donation eligibility date and locate daily mobile blood drives near their current location, for example. Using the application, a donor can schedule his or her next donation using a "make appointment" function, or place a direct call to the blood center, if the donor prefers. Using the application, a blood center can connect with donors frequently but not in a manner that will be perceived as intrusive. Potentially, donor frequency can increase. In some examples, incentives can be provided through participation to help increase donation frequency. Donor access and scheduling can be tracked by call center staff, application reports, etc. Donor activity can be tracked via spreadsheet, one or more data fields in customer relationship management (CRM) software, etc.

In some examples, donor appointments can be tied to electronic calendars (e.g., Outlook™, Google™, etc.) via the phone application.

In some examples, an example application may be provided for donors to use to keep track of when, where, and/or what they last donated (plasma, red blood cells, etc.). This application may have reminders built into the application and enable donors to set reminders as they like.

In some examples, an application may be integrated with a phone's (e.g., an iPhone™) built-in calendar or other calendars so users can keep their donation appointments with their other calendar data. In some examples, general donation information such as why someone should donate, some information about blood types, etc. may be provided by the application.

In some examples, an application reminds donors that it is time to donate blood, plasma, etc. again. In some examples, the application determines and/or checks the next time that the donor can donate. In some examples, an application records, stores and/or accesses information relating to previous donations and conveys this information to the donor.

In some examples, an application may serve as a scheduling assistant. The application can sort the contacts list by key data such as deferral dates or recommended procedure type, for example.

In some examples, an application may use a phone's location services to help and/or enable a donor find a local donation center.

In some examples, a donor's particular information can be segmented from other donor information. In some examples, donor information for one blood center can be segmented from donor information for other blood centers. Data requests, such as a time taken for a donor to return to give blood after he or she is again eligible (e.g., a number of days after becoming eligible), donor frequency data by age segment, and/or other data can be determined and retrieved via the application.

In some examples, application icon(s) can be customized based on blood center, donor, and/or other characteristic. A data countdown until donor appointment and/or donor eligibility can be visible via the icon. Donor health information and/or other information for the donor can be provided by the application via icon(s), graphics, text, etc.

In some examples, the application can enable blood centers to conduct segmented pushes to donors that have particular blood type(s).

Mobile Operator Application

In some examples, an application can give visual assistance in operating an Alyx™ system or an Amicus™ separator. In some example, the application may provide a mobile version of the operator's manual for an Alyx™ system or an Amicus™ separator.

In some examples, an application may make provider websites mobile-friendly. For example, Microsoft SharePoint™ supports mobile views and can be leveraged to provide a mobile-friendly provider (e.g., Fenwal) website.

Figure 21:
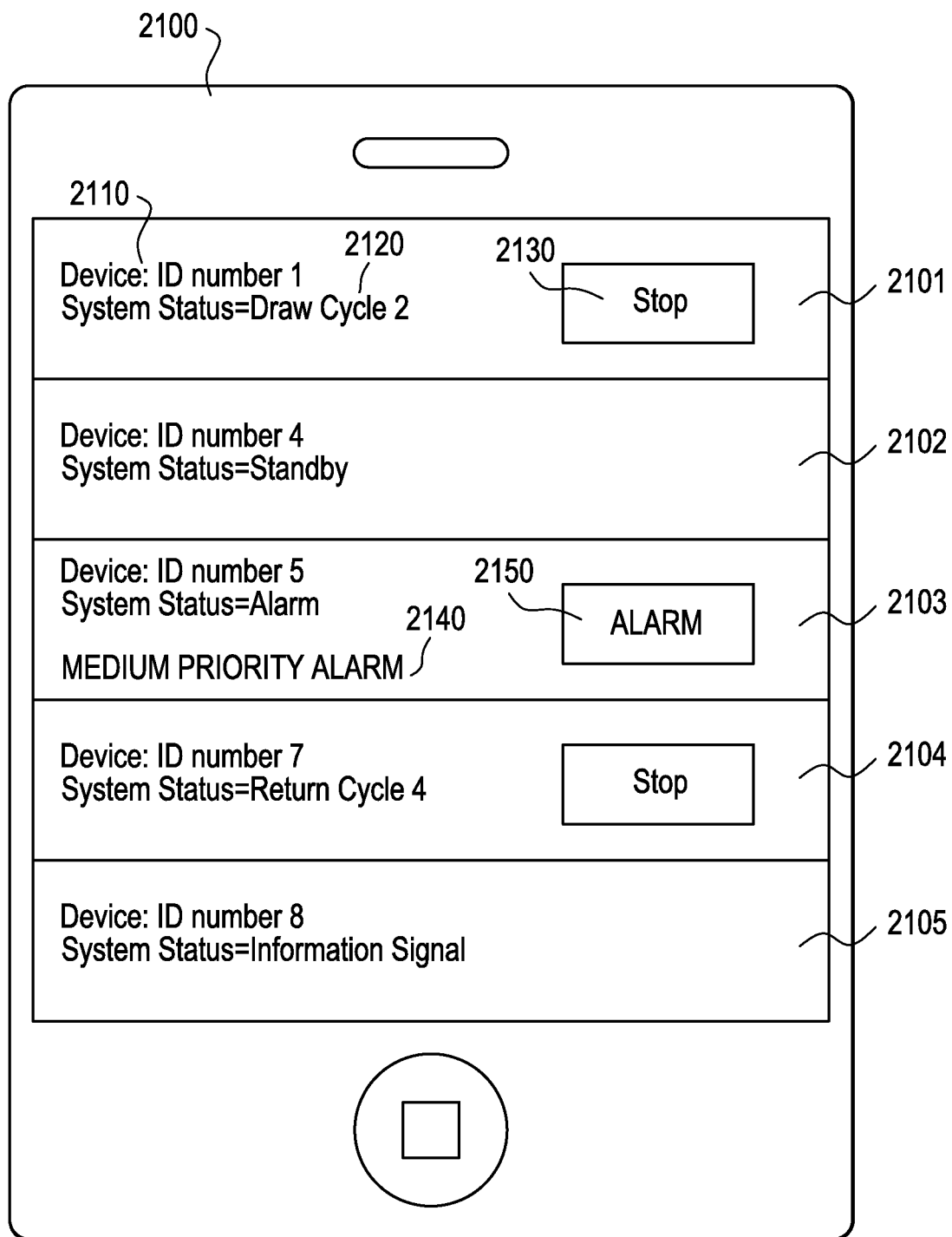
FIG. 21 depicts an example mobile device including an interface listing one or more blood collection/processing instruments under control of the operator.

FIG. 21 depicts an example mobile device 2100 including an interface listing one or more blood collection/processing instruments 2101, 2102, 2103, 2104, 2105 under control of the operator. A device identifier 2110 and status 2120 is provided for each instrument 2101-2105. A control 2130 can be provided to stop operation of the instrument 2101-2105, for example. If an alarm has been triggered at an instrument 2101-2105, an indication of the alarm 2140 can be provided as well as an option for additional alarm information 2150.

Thus, using the example mobile interface of FIG. 21, system status for all collection systems in a network can be provided to a mobile device 2100, such as an iPhone™, iPad™, BlackBerry™, and the like. The status can include an instrument number, status, etc., and can provide quick access to one or more features such as a stop feature, an alarm feature, etc. The mobile device 2100 can be used as a mobile monitor rather than tying an operator to a stationary desktop or computer system.

In certain examples, the mobile device 2100 can provide a practice forum for training new operators regarding configuration, use, and/or troubleshooting of blood collection instrument(s). For example, step-by-step photos, diagrams, and instructions can be shown for proper kit loading for one or more devices. Access to on-line operator's manuals, error codes, and/or product information can be provided via keyword search through the mobile device 2100. In certain examples, complaints can be submitted via the mobile device interface 2100. In certain examples, troubleshooting of instrument operation can be facilitated using the mobile device 2100.

Reporting Application

In some examples, an application enables a blood center and/or blood center personnel to report an issue (e.g., problem, complaint, etc.) to a provider (e.g., Fenwal).

Certain examples provide complaint reporting. Rather than a paper report, an operator who experienced an issue first-hand can submit a report and improve a likelihood of including important detail. The operator can register the complaint first hand and incorporate product bar code scans and photos that may be important to a complaint investigation. Pre-population of information can streamline the complaint reporting process, and automatically submitting the report to a vendor via the mobile device 2100 can help save the trouble and time of faxing the document. Automatic assignment of a complaint number provides improved ability to track the complaint through to resolution.

In certain examples, an instrument trouble shooting decision tree can improve a speed with which an operator is able to resolve an issue rather than potentially delay to make a phone call and find an appropriate person with whom to speak. Also, submitting a service request can be more easily facilitated via the mobile device 2100.

In certain examples, a camera associated with the mobile device 2100 can be used to scan a product barcode as well as record and submit photo(s) of a complaint issue with the product to facilitate complaint description and filing. The camera can be used to record and submit instrument screen photo(s) with associated error code(s). Barcode scanning of the product retrieves a correct product complaint form that has been pre-populated with product information. The mobile interface can be used to additionally pre-populate the complaint form with center information, date, time, complaint reference number, etc. The mobile device 2100 can be used to submit the complaint directly to the instrument vendor with an option to copy the blood center's e-mail for local tracking, for example.

An additional feature can be an instrument trouble shooting decision tree similar to the practice currently used orally via instrument vendor customer service. The decision tree can help the operator 1) resolve the issue or 2) submit a service request either by a) embedded form or b) leading the user to call customer service directly from the mobile application.

Cost Analysis Application

In some examples, an application compares how much a donor can make by donating certain blood components over a certain period of time. For example, a donor may make more money donating plasma versus donating whole blood. For example, a donor may make more money donating a certain amount of whole blood and a certain amount of plasma. In some examples, the donor can determine if he or she can make more money over six months by donating plasma or platelets.

In some examples, rather than being paid for a donation, a donor can be offered different incentives (e.g., coupons, discounts, recognition, and/or other prize) to continue regular donations over time. Donations until a next incentive can be tracked and displayed to the donor, for example.

Example Application Having a Game Style Interface

In some examples, an application is a video game that enables donors to advance to different levels based on the amount of blood donated. For example, the application may be a video game where a character (e.g., Fenny the red blood cell) has to jump from level to level until reaching a new donor and saving his/her life.

Application Used in Connection with Blood Donation

In some examples, an application is provided that a phlebotomist could use as a humorous tool to help break the ice with a new donor. In some examples, the application may be a vein finder set up much like a stud finder and would beep when paced over a supposedly large vein in the donor's arm.

Blood Processing Application and/or Blood Donation Application

In some examples, an application can display and/or provide information regarding units of platelets, milliliters of plasma given, one or two units of RBC, etc. In some examples, an application may display and/or provide information regarding which arm of a donor was used (e.g., draw and return). For example, the application can display which donor arm was used the last time the donor donated and/or a number of times a particular arm has been used to donate.

In some examples, an application can display and/or provide information regarding a next eligible donation date based on an amount of platelets, plasma and/or red blood cells donated. In some examples, an application can display and/or provide information regarding using special features, registering to a provider server (e.g., a Fenwal server) when donated on a provider's instrument (e.g., Amicus™ or ALYX™) for a reward program, such as iTunes™ music by accumulating points.

In some examples, an application includes three main sections; however, any other number of or different sections may be used instead. The sections can include a personal information section including last donation information, eligible date information, current donation information including any medical information that can be obtained from a donation site such as blood pressure, pulse, etc., for example. A donation type (such as whole blood (WB), platelets (Plt), plasma, two-RBC, etc.) can also be provided.

A second section can feature a location at which the donation is happening (e.g., this week), particularly via mobile collection. Collection sites can be listed and, when selected, a site will be displayed including information regarding the blood drive, for example. A link to an electronic map, such as a Google™ map, can be leveraged to show the route from current position which is available through a global positions system (GPS) and/or other positioning system, for example.

A third section can include a registration page for a provider (e.g., Fenwal) web site. Every time one donates on a Fenwal device, for example, one can register at the Fenwal site or other affiliated provider. Registration can be done at the donation site, and the registration can record the GPS information of the location authenticating the donation. A user can also provide a "key" through the blood collection agency for authentication by way of the application.

Data Management System and/or Catalog Application

In some examples, an application enables the catalog of products (e.g., Fenwal products) by selecting the product family and code number and the application will provide a complete product description such as quantity of bags in the set, type of sampling system, filter type (if applicable), solution types and volumes, etc; providing an electronic form to order products from customer service; and/or providing a database to track inventory levels by code/lot number/expiration date as products are received and shipped out to other centers or on mobile drives.

Product Surveillance System

In some examples, an application enables product surveillance by snapping a picture of product defects and enabling a questionnaire(s) to be filled out; enabling complaints to be sent electronically to product surveillance; and/or receiving instructions on how to return the product for complaint investigation.

Mobile Process Flows

Figure 22:
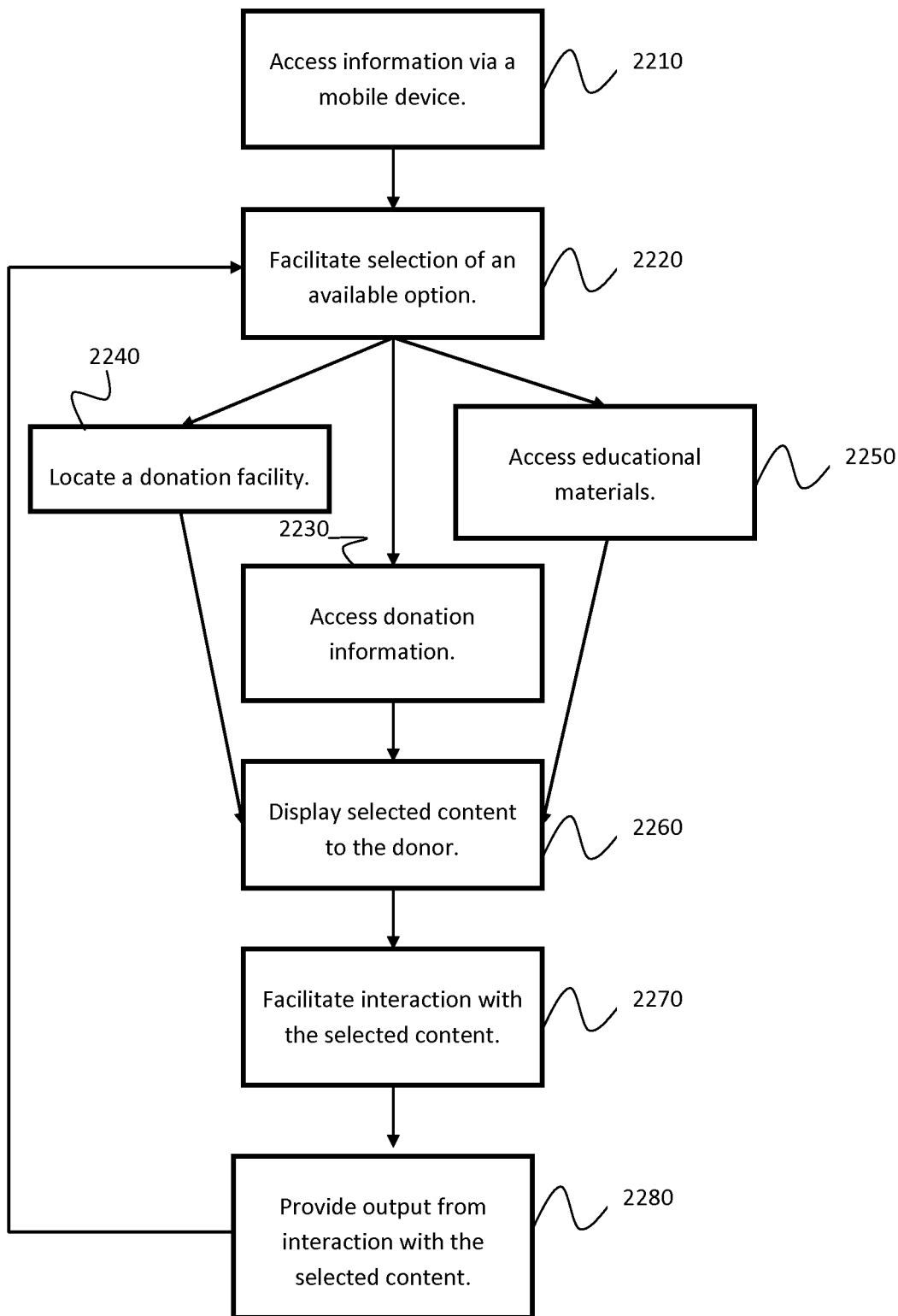
FIGS. 22-24 provide flow diagrams for methods for donors, operators, and administrators to review and manage blood collection and associated instrument information.
Figure 23:
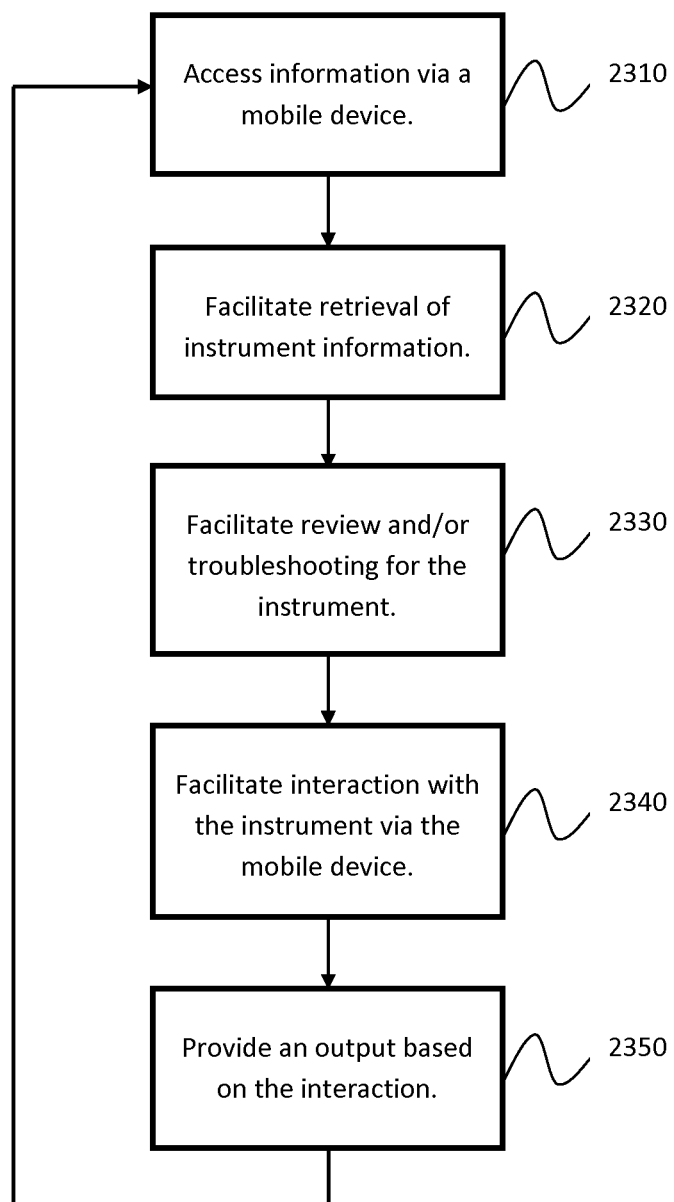
Figure 24:
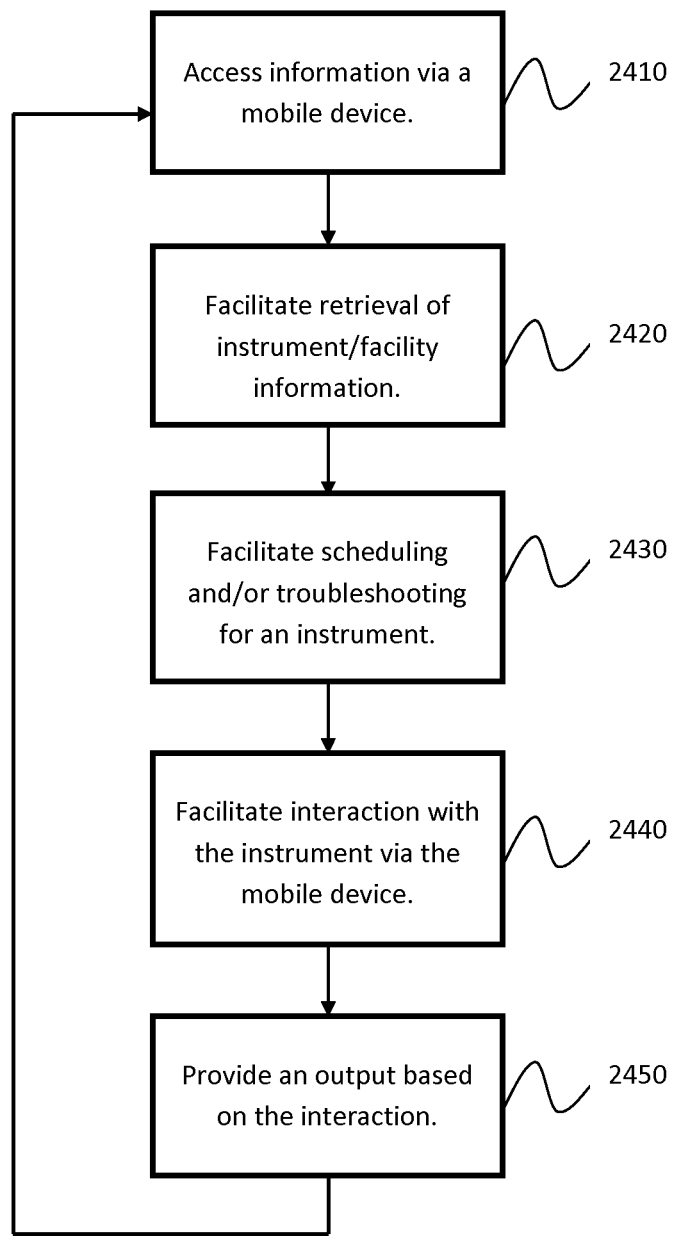

FIGS. 22-24 provide flow diagrams for methods for donors, operators, and administrators to review and manage blood collection and associated instrument information. FIGS. 22-24 depict example flow diagrams representative of processes that may be implemented using, for example, computer readable instructions that may be used during blood collection operator training. The example processes of FIGS. 22-24 may be performed using a processor, a controller and/or any other suitable processing device. For example, the example processes of FIGS. 22-24 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIGS. 22-24 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 22-24 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 22-24 may be implemented manually or as any combination(s) of any of the foregoing techniques, for example, any combination of firmware, software, discrete logic and/or hardware. Further, although the example processes of FIGS. 22-24 are described with reference to the flow diagrams of FIGS. 22-24, other methods of implementing the processes of FIGS. 22-24 may be employed. For example, the order of execution of the blocks may be changed, and/or some of the blocks described may be changed, eliminated, sub-divided, or combined. Additionally, any or all of the example processes of FIGS. 22-24 may be performed sequentially and/or in parallel by, for example, separate processing threads, processors, devices, discrete logic, circuits, etc.

FIG. 22 provides a flow diagram 2200 for a method for donor access to blood collection information. At block 2210, a donor accesses blood collection information via a mobile device. The donor can be provided with a variety of information and functionality, such as facility location, donation information, educational resources, etc. At block 2220, the donor selects an available option. At block 2230, the donor views his or her donation information via the mobile device. At block 2240, the donor locates a donation facility via the mobile device. At block 2250, the donor accesses training/educational materials via the mobile device.

At block 2260, selected content is displayed to the donor via the mobile device. For example, donation information is shown, a donation facility is mapped, and/or educational materials are displayed for review and/or interaction. At block 2270, the donor can interact with the displayed content. At block 2280, based on the interaction, an output is provided from the mobile device. For example, donation information can be updated, an appointment can be made, results can be sent, etc. The method can be executed in accordance with many examples, including examples described above.

FIG. 23 provides a flow diagram 2300 for a method for operator access to blood collection information. At block 2310, an operator accesses blood collection instrument information via a mobile device. At block 2320, blood instrument information is retrieved for operator review at the mobile device. At block 2330, the operator can review and/or troubleshoot the instrument via the mobile device. At block 2340, the operator can interact with the instrument via the mobile device. At block 2350, the mobile device provides an output based on the operator interaction with the instruction. The method can be executed in accordance with many examples, including examples described above.

FIG. 24 provides a flow diagram 2400 for a method for administrator access to blood collection information. At block 2410, an administrator accesses blood collection facility information via a mobile device. At block 2420, blood collection facility and/or instrument information is retrieved for administrator review via the mobile device. At block 2430, the administrator can perform a variety of activities, such as troubleshooting, scheduling, etc., with respect to one or more blood collection instruments in the facility. At block 2440, the administrator can interact with the one or more instruments via the mobile device. At block 2450, the mobile device provides an output based on the administrator interaction with the facility. The method can be executed in accordance with many examples, including examples described above.

Bar Code Data Bridge

Figure 25:
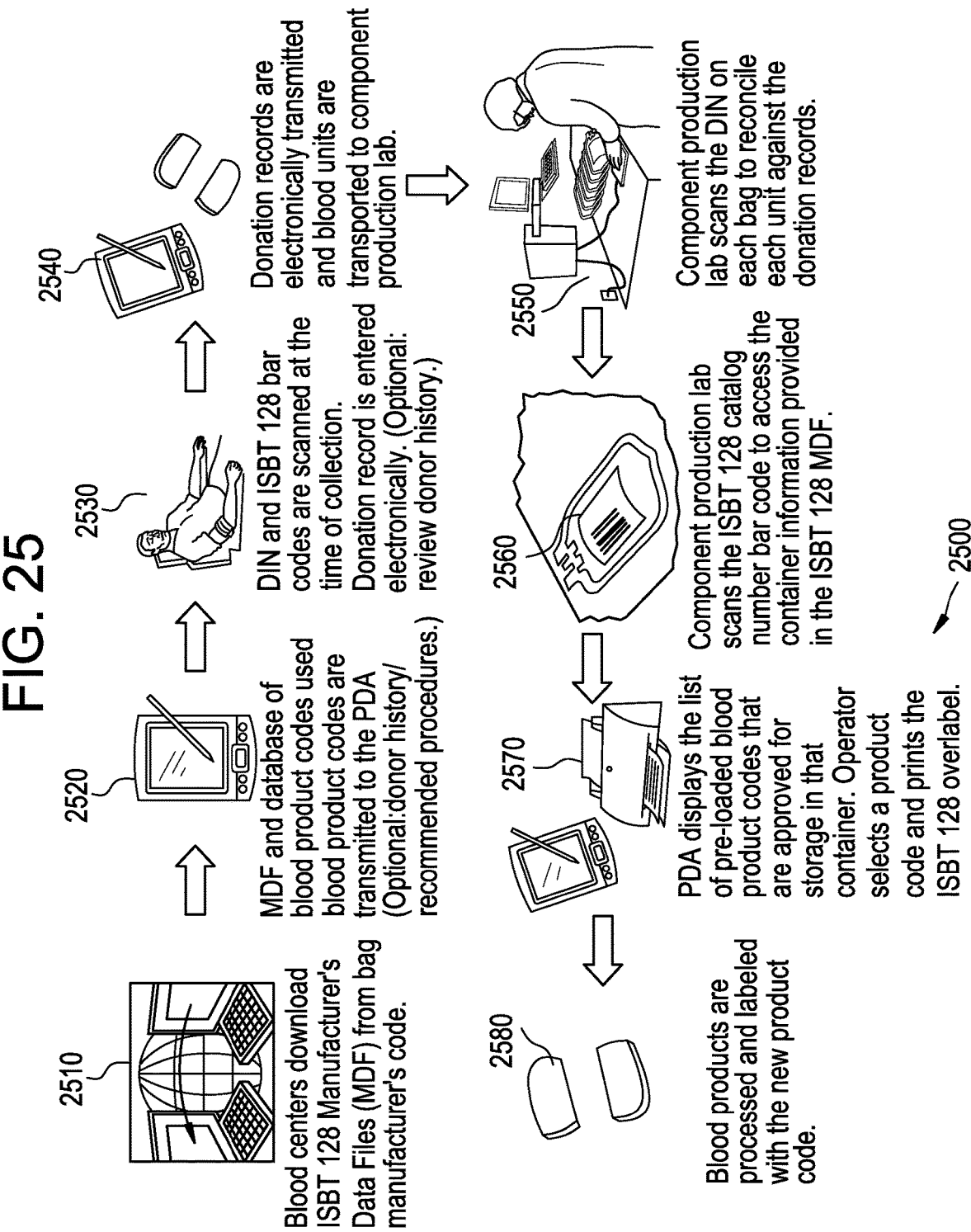
FIG. 25 depicts an example process flow demonstrating how blood products can be processed and labeled with new product codes.

FIG. 25 relates to a bar code data bridge. The bar code data bridge can be used in conjunction with a mobile computing device, such as an iPhone™, iPad™, Black-Berry™, Android phone, etc., with a scanner or camera to capture the bar code information. The bar code data bridge can operate in conjunction with a donor, operator, and/or administrator application or interface as described above.

In some examples, a "Transition Label" for blood containers may contain both Codabar and ISBT 128 bar codes to meet the needs of U.S. blood centers during the industry's conversion from Codabar to ISBT 128 labeling standards. Many data management software packages are currently designed to use Codabar bar code information and are not yet able to interpret the ISBT128 Manufacturer's Data Files that provide certain process control information for the blood centers. In some cases, providers may decide to convert to "full format" ISBT 128 labels without the Codabar information. If this occurs before data management software is updated to utilize the ISBT 128 data files, blood centers may lose certain process control information on the labels. U.S. Pat. No. 7,588,193, incorporated by reference herein in its entirety, is co-owned with the present application by Fenwal, Inc., and provides example of a blood component container label including at least one bar code based on a first bar code format and another bar code based on a second bar code format.

In some examples, handheld personal digital assistants (PDAs) (e.g., iPhone™, etc.) with bar code scanners are utilized to decode ISBT 128 bar codes and display important process control information for the set that is contained within ISBT 128 Manufacturer's Data Files that are electronically distributed by the blood bag manufacturers.

In some examples, the donor ID bar code is scanned from donor registration paperwork to access database of donor history. For example, the PDA can be loaded with a database of donor records.

In some examples, an electronic donation record is created and/or blood bag and/or kit bar codes to record code, lot, and/or other information is scanned.

In some examples, a PDA is connected to a computer to transmit donation records to a component processing lab.

In certain examples, a PDA can be connected to one or more small portable printers to print ISBT 128 blood product code labels on demand (e.g., the PDA is loaded with a database of ISBT 128 product codes used by the blood center), for example.

In some examples, a software patch may be provided to link the GTIN (GS 1 Global Trade Item Number) contained in the ISBT 128 Manufacturer's Data Files to inventory control systems to trigger new orders of SPUs or kits when supplies are low.

In some examples, the application reduces or minimizes paperwork and errors at the blood collection center, and helps identify new candidates for automated procedures based on donor history.

In some examples, the application helps improve labor efficiency at the component processing lab and automates the reconciliation process for incoming products.

In some examples, the application reduces or minimizes the amount of discarded blood products that are not processed within the allowable timeframe.

In some examples, the application reduces or minimizes label inventory and scrap for preprinted ISBT 128 product codes at the component processing lab.

In some examples, the application helps improve patient safety by preventing component processing errors.

In some examples, the application helps prevent blood processing unit (BPU)/kit inventory stock-outs at blood centers.

The application may include an over-labeling aspect of the process. In some examples, the application may include different scanning points (e.g., at cooler/truck/centrifuge).

In some examples, the product bar codes may no longer be on the base label because the use of the manufacture's data files may eliminate a need for the product bar codes.

As shown in FIG. 25, a process flow 2500 demonstrates how blood products can be processed and labeled with new product codes. At 2510, a blood center downloads one or more manufacturer data files (MDFs) (e.g., ISBT 128 manufacturer data files) from a blood bag manufacturer's website. At 2520, an MDF and a database of blood product codes used by the blood center are transmitted to a mobile computing device. In certain examples, donor history and/or recommended procedures (e.g., for the particular donor, desired inventory, etc.) are transmitted as well.

At 2530, bar codes (e.g., donor identification and blood bag bar codes) are scanned at a time of blood collection. A donation record is entered electronically. A donor history may be reviewed as well, for example. At 2540, donation record(s) are electronically transmitted and blood unit(s) are transported to a component production laboratory, for example.

At 2550, the component production lab scans the donor identification number on each bag to reconcile each unit against the donation record(s). At 2560, the component production lab scans the manufacturer catalog number bar code (e.g., ISBT 128) to access container information provided in the MDF (e.g., the ISBT 128 MDF).

At 2570, the mobile computing device displays a list of pre-loaded blood product code(s) approved for storage in the selected container. The operator selects a product code and prints an overlabel (e.g., an ISBT 128 overlabel), for example. At 2580, blood product(s) are processed and labeled with the new product code.

Figure 26:
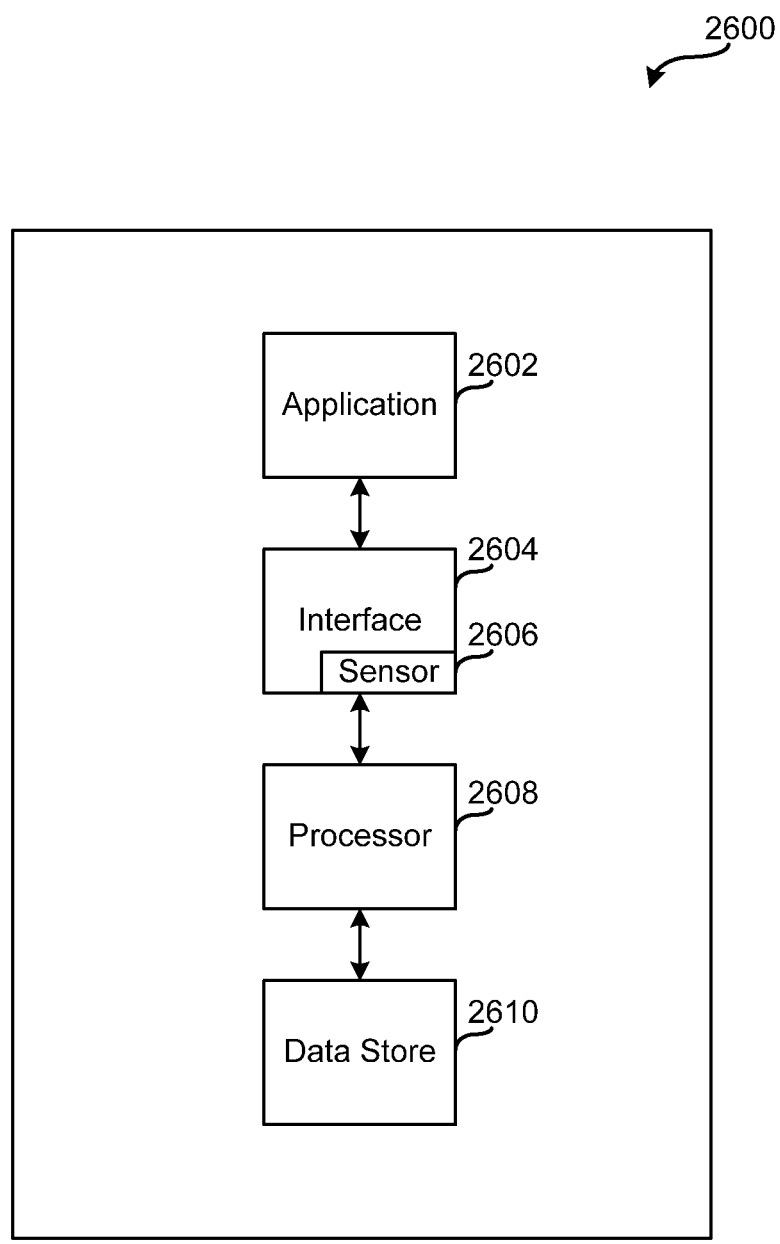
FIG. 26 is a block diagram of an example system or mobile device.

FIG. 26 is a block diagram of an example system or mobile device 3600 including an application 3602, an interface 2604 including a sensor(s) 2606, a processor 2608 and a data store 2610. The example system 2600 may be used to implement the example mobile devices described above, for example. While an example manner of implementing the mobile device 100, 600, 700, 900, 1200, 1300, 2100, etc., has been illustrated in FIG. 26, one or more of the elements, processes and/or devices illustrated in FIG. 26 may be combined, divided, re-arranged, omitted, eliminated and/or implemented in other ways.

The application 2602, the interface 2604, the sensor 2606, the processor 2608 and/or the data store 2610 and, more generally, the example system 2600 may be implemented by hardware, software, firmware and/or a combination of hardware, software and/or firmware. Thus, the application 2602, the interface 2604, the sensor 2606, the processor 2608 and/or the data store 2610 and, more generally, the example system 2600 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the application 2602, the interface 2604, the sensor 2606, the processor 2608 and/or the data store 2610 and, more generally, the example system 2600 are hereby expressly defined to include a tangible medium such as a memory, DVD, CD, Blu-ray, etc., storing the software and/or firmware. Further still, the example system 2600 of FIG. 26 may include one or more elements, processes and/or devices in addition to, or instead of, those illustrated in FIG. 26, and/or may include more than one of any or all of the illustrated elements, processes and devices.

The application 2602 may include instructions that, when driven by the processor 2608, cause the processor 2608 to retrieve data, tutorial information, audio, graphics, text, etc. and display the same using the interface 2604. For example, based on the initiation of a tutorial session, the application 2602 may cause a video to be displayed on the interface 2604 on how to operate and/or troubleshoot a blood processing instrument. The application 2602 may cause instructions to be displayed on the interface 2604 on how to participate in the tutorial. In some examples, based on the system 2600 identifying the user's experience level, a different tutorial and/or information may be displayed. The system 2600 may identify the user's experience level from data stored at the data store 2610 and/or based on input received from the user.

Based on the information received, the processor 2608 may generate feedback that may be displayed at the interface 2604 and/or stored at the data store 2610. Once the processor 2608 determines that the tutorial is complete, the processor 2608 may generate feedback relating to the user's performance, etc. While the data store 2610 is depicted as being within the system 2600, the data store 2610 may be at a different location (e.g., a remote location).

The processor 2608 may drive the interface 2604 to provide information and/or functionality to the user. In some examples, the interface 2604 may be configured as a graphical user interface (GUI). The GUI may be touch pad/screen integrated with the system 2600. The system 2600 may include one or more internal memories and/or data stores including the data store 2610. Data storage can include any variety of internal and/or external memory, disk, remote storage communicating with the system 2600.

Figure 27:
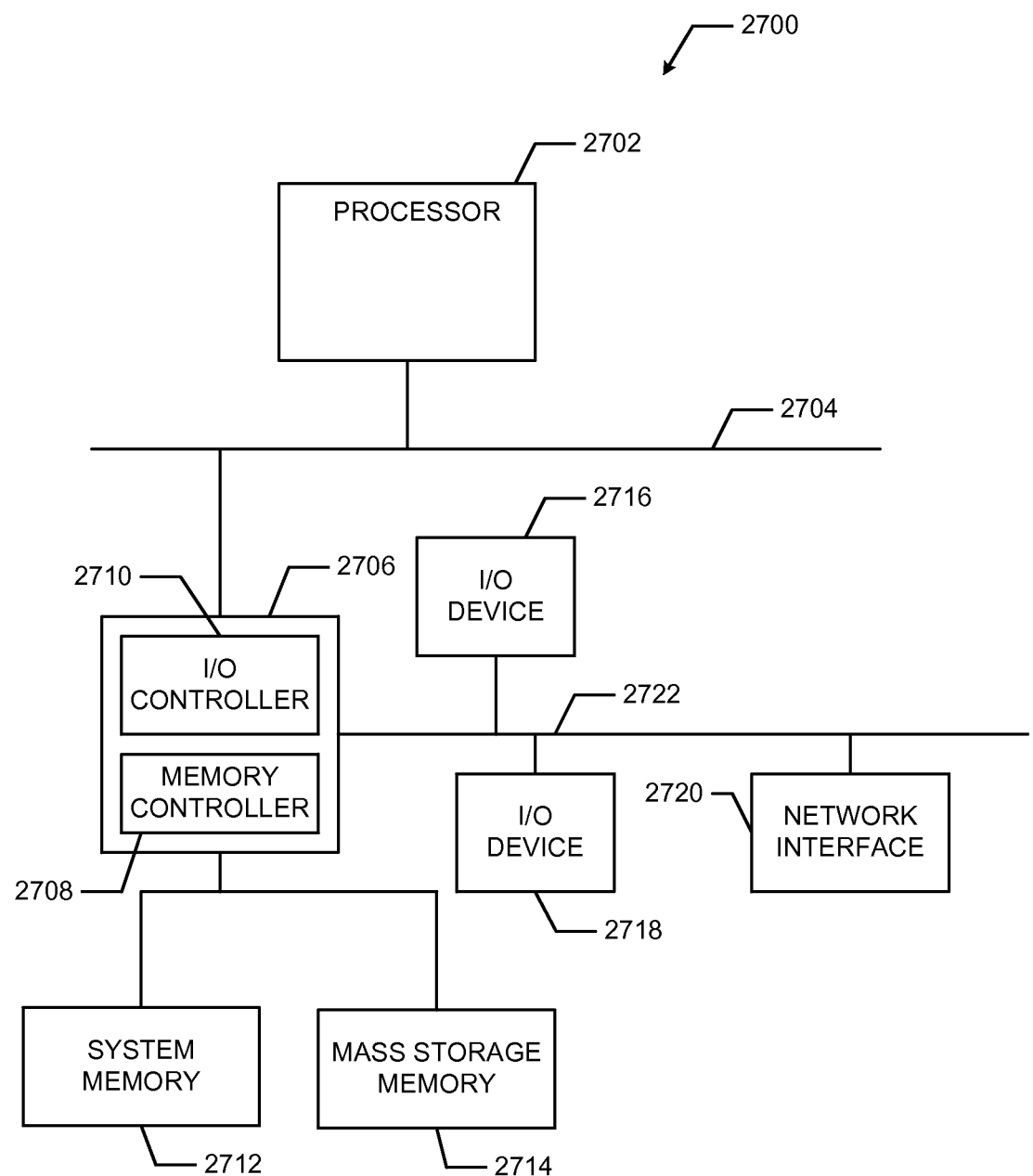
FIG. 27 is a block diagram of an example processor system that can be used to pump, implement, control and/or drive the systems and methods described herein.

FIG. 27 is a block diagram of an example processor system 2700 that can be used to pump, implement, control and/or drive the systems and methods described herein. As shown in FIG. 27, the processor system 2700 includes a processor 2702 that is coupled to an interconnection bus 2704. The processor 2702 may be any suitable processor, processing unit or microprocessor. Although not shown in FIG. 27, the processor system 2700 may be a multi-processor system and, thus, may include one or more additional processors that are identical or similar to the processor 2702 and that are communicatively coupled to the interconnection bus 2704.

The processor 2702 of FIG. 27 is coupled to a chipset 2706, which includes a memory controller 2708 and an input/output (I/O) controller 2710. As is well known, a chipset typically provides I/O and memory management functions as well as a plurality of general purpose and/or special purpose registers, timers, etc. that are accessible or used by one or more processors coupled to the chipset 2706. The memory controller 2708 performs functions that enable the processor 2702 (or processors if there are multiple processors) to access a system memory 2712 and a mass storage memory 2714.

The system memory 2712 may include any desired type of volatile and/or non-volatile memory such as, for example, static random access memory (SRAM), dynamic random access memory (DRAM), flash memory, read-only memory (ROM), etc. The mass storage memory 2714 may include any desired type of mass storage device including hard disk drives, optical drives, tape storage devices, etc.

The I/O controller 2710 performs functions that enable the processor 2702 to communicate with peripheral input/output (I/O) devices 2716 and 2718 and a network interface 2720 via an I/O bus 2722. The I/O devices 2716 and 2718 may be any desired type of I/O device such as, for example, a keyboard, a video display or monitor, a mouse, etc. The network interface 2720 may be, for example, an Ethernet device, an asynchronous transfer mode (ATM) device, an 802.11 device, a DSL modem, a cable modem, a cellular modem, etc. that enables the processor system 2700 to communicate with another processor system.

While the memory controller 2708 and the I/O controller 2710 are depicted in FIG. 27 as separate blocks within the chipset 2706, the functions performed by these blocks may be integrated within a single semiconductor circuit or may be implemented using two or more separate integrated circuits.

Certain examples can include processes that can be implemented using, for example, computer readable instructions that can be used to facilitate mobile blood applications for donors, operators, administrators, and/or providers. The example processes can be performed using a processor, a controller and/or any other suitable processing device. For example, the example processes can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes can be implemented using coded instructions (e.g., computer readable instructions) stored on a non-transitory computer readable medium such as a flash memory, a read-only memory (ROM), a random-access memory (RAM), a CD, a DVD, a Blu-ray, a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes can be implemented manually or as any combination(s) of any of the foregoing techniques, for example, any combination of firmware, software, discrete logic and/or hardware. Further, although example processes may be described with reference to a particular order and/or structure, other methods of implementing the processes may be employed. For example, the order of execution of the blocks can be changed, and/or some of the blocks described may be changed, eliminated, sub-divided, or combined. Additionally, any or all of the example processes can be performed sequentially and/or in parallel by, for example, separate processing threads, processors, devices, discrete logic, circuits, etc.

While particular embodiments of the invention have been shown and described, it will be obvious to those skilled in the art that changes and modifications may be made therein without departing from the invention in its broader aspects.

The invention claimed is:

1. A computer-implemented method for medical instrument management using a handheld mobile device comprising a phone, said method comprising:
providing on the handheld mobile device an application downloaded and installed on the device by a customer, the application causing the handheld mobile device to provide a graphical representation of one or more medical instruments, at least one of the medical instruments being configured to use a needle in a procedure, with a visual indication of a status for each instrument, the graphical representation visually conveying information regarding each of the one or more medical instruments and selectable by a user to provide additional information regarding each of the one or more medical instruments;
the application facilitating access to interact with the one or more medical instruments via the handheld mobile device, interaction between the handheld mobile device and the one or more medical instruments to include access to medical instrument controls via the handheld mobile device to interact with an alarm feature which was triggered at each instrument and a stop feature for each instrument; and
the application updating the visual indication of the status for each instrument, the application configured to provide an icon representative of the application on a main screen of the phone in a location so as not to interfere with at least one other main screen feature.

2. The method of claim 1, wherein facilitating further comprises facilitating troubleshooting of an alarm at one of the one or more medical instruments via at least one of an entered alarm code and a capture image of an alarm condition.

3. The method of claim 1, wherein providing further comprises displaying a floorplan of a plurality of medical instruments on the handheld mobile device, each of the plurality of medical instruments represented by a graphical representation.

4. The method of claim 1, further comprising displaying an inventory of available blood products for a blood collection facility and facilitating inventory control via the mobile device.

5. The method of claim 4, wherein facilitating inventory control further comprises facilitating review and update of blood component collection goals via the mobile device.

6. The method of claim 4, further comprising transmitting a targeted donation request based at least in part on the review and update of blood component collection goals.

7. The method of claim 1, further comprising providing training to an instrument operator via the mobile device.

8. The method of claim 1, further comprising collecting and reporting an operator complaint via the mobile device.

9. The method of claim 1, further comprising facilitating product and donor matching via at least one of an entered value and a captured image using the mobile device.

10. The method of claim 1, further comprising tracking a time of a collected blood component in transit using the mobile device, the mobile device connected to a container to transmit the collected blood component.

11. The method of claim 1, further comprising facilitating reading of a bar code at a point of collection using the mobile device, the bar code including at least two bar codes in different formats for identifying and tracking a collected blood component.

12. A tangible computer readable storage medium including program code for execution by a processor, the program code, when executed, to implement a method for medical instrument management, said method comprising:
providing on a handheld mobile device a graphical representation of one or more medical instruments, at least one of the medical instruments being configured to use a needle in a procedure, with a visual indication of a status for each instrument, the graphical representation visually conveying information regarding each of the one or more medical instruments and selectable by a user to provide additional information regarding each of the one or more medical instruments;
facilitating access to interact with the one or more medical instruments via the handheld mobile device, interaction between the mobile device and the one or more medical instruments to include access to medical instrument controls via the handheld mobile device to interact with an alarm feature for each instrument and a stop feature for each instrument; and
updating the status for each instrument.

13. The computer readable storage medium of claim 12, wherein facilitating further comprises facilitating troubleshooting of an alarm at one of the one or more medical instruments via at least one of an entered alarm code and a capture image of an alarm condition.

14. The computer readable storage medium of claim 12, wherein providing further comprises displaying a floorplan of a plurality of blood collection instruments, each of the plurality of blood collection instruments represented by a graphical representation.

15. The computer readable storage medium of claim 12, further comprising displaying an inventory of available blood products for a blood collection facility and facilitating inventory control via the mobile device.

16. The computer readable storage medium of claim 15, wherein facilitating inventory control further comprises facilitating review and update of blood component collection goals via the mobile device.

17. The computer readable storage medium of claim 15, further comprising transmitting a targeted donation request based at least in part on the review and update of blood component collection goals.

18. The computer readable storage medium of claim 12, further comprising providing training to an instrument operator via the mobile device.

19. The computer readable storage medium of claim 12, further comprising collecting and reporting an operator complaint via the mobile device.

20. The computer readable storage medium of claim 12, further comprising facilitating product and donor matching via at least one of an entered value and a captured image using the mobile device.

21. The computer readable storage medium of claim 12, further comprising tracking a time of a collected blood component in transit using the mobile device, the mobile device connected to a container to transmit the collected blood component.

22. The computer readable storage medium of claim 12, further comprising facilitating reading of a bar code at a point of collection using the mobile device, the bar code including at least two bar codes in different formats for identifying and tracking a collected blood component.

23. A mobile medical instrument management system comprising:
   a medical instrument configured to use a needle in a procedure performed on a patient;
   a handheld mobile device comprising a display, an input device, a processor and memory storing instructions to display content and accept user input to implement:
   a graphical representation of one or more medical instruments provided on the display, at least one of the medical instruments being the medical instrument configured to use a needle in a procedure performed on a patient, including a visual indication of a status for each instrument, the graphical representation to visually convey information regarding each of the one or more medical instruments and selectable by a user via the input device to provide additional information regarding each of the one or more medical instruments; and
   an executable application embodied on the memory to provide access to interact with the one or more medical instruments via the input device of the handheld mobile device, interaction between the handheld mobile device and the one or more medical instruments to include access to medical instrument controls via the mobile device to interact with an alarm feature which was triggered at each instrument and a stop feature for each instrument, the system to update the status for each instrument.

24. The system of claim 23, wherein the application is to facilitate troubleshooting of an alarm at one of the one or more medical instruments via at least one of an entered alarm code and a capture image of an alarm condition.

25. The system of claim 23, wherein the graphical representation further comprises a displayed floorplan of a plurality of blood collection instruments, each of the plurality of blood collection instruments represented by a graphical representation.

26. The system of claim 23, further comprising an inventory display showing available blood products for a blood collection facility, the application to facilitate inventory control for the blood collection facility via the mobile device.

27. The system of claim 26, wherein the application is to facilitate review and update of blood component collection goals via the mobile device.

28. The system of claim 27, wherein the application is to transmit a targeted donation request based at least in part on the review and update of blood component collection goals.

29. The system of claim 23, further comprising interactive education materials to provide training to an instrument operator via the mobile device.

30. The system of claim 23, wherein the application is to collect and report an operator complaint via the mobile device.

31. The system of claim 23, wherein the application is to facilitate product and donor matching via at least one of an entered value and a captured image using the mobile device.

32. The system of claim 23, wherein the application is to track a time of a collected blood component in transit using the mobile device, wherein the mobile device is to be connected to a container used to transmit the collected blood component.

33. The system of claim 23, wherein the mobile device further comprises a camera or scanner to facilitate reading of a bar code at a point of collection using the mobile device, the bar code including at least two bar codes in different formats for identifying and tracking a collected blood component.

34. The system of claim 23, wherein the medical instrument is a blood component collection machine, wherein the handheld mobile device is a smart phone, wherein the graphical representation is provided by an application downloaded by a user, the application configured to provide an icon representative of the application on a main screen of the phone in a location so as not to interfere with at least one other main screen feature.

* * * * *